(12) United States Patent
Peak et al.

(10) Patent No.: US 8,510,133 B2
(45) Date of Patent: Aug. 13, 2013

(54) INSURANCE PROCESSING SYSTEMS AND METHODS USING MOBILE DEVICES FOR MEDICAL MONITORING

(75) Inventors: David F. Peak, Avon, CT (US); Andrew J. Amigo, Gloucester, MA (US); Richard M. Borden, West Hartford, CT (US); Keven J. Busque, Manchester, CT (US); Christopher Graham, Eden Prairie, MN (US); Eugene J. Walters, Avon, CT (US)

(73) Assignee: Hartford Fire Insurance Company, Hartford, CT (US)

( * ) Notice: Subject to any disclaimer, the term of this patent is extended or adjusted under 35 U.S.C. 154(b) by 154 days.

(21) Appl. No.: 12/816,025

(22) Filed: Jun. 15, 2010

(65) Prior Publication Data

US 2011/0161100 A1    Jun. 30, 2011

Related U.S. Application Data

(60) Provisional application No. 61/291,501, filed on Dec. 31, 2009.

(51) Int. Cl.
*G06Q 40/00* (2012.01)

(52) U.S. Cl.
USPC ........................................ 705/4; 705/2; 705/3

(58) Field of Classification Search
USPC .......................................................... 705/2–4
See application file for complete search history.

(56) References Cited

U.S. PATENT DOCUMENTS

| | | | |
|---|---|---|---|
| 2007/0038478 A1* | 2/2007 | Kay ................................. | 705/4 |
| 2007/0043594 A1* | 2/2007 | Lavergne ......................... | 705/2 |
| 2009/0119133 A1* | 5/2009 | Yeransian et al. ............... | 705/4 |
| 2010/0131303 A1* | 5/2010 | Collopy et al. .................. | 705/4 |
| 2010/0174564 A1 | 7/2010 | Stender et al. | |

* cited by examiner

*Primary Examiner* — Michelle Le
(74) *Attorney, Agent, or Firm* — Buckley, Maschoff & Talwalkar LLC

(57) ABSTRACT

Pursuant to some embodiments, systems, methods and devices are provided for insurance processing including installing a medical monitoring application associated with a user of a mobile device, the medical monitoring application including configuration data associated with at least a first medical monitoring rule, displaying, under control of the medical monitoring application, a series of instructions to cause the mobile device to be configured to communicate with at least a first biometric sensor, collecting, based on the at least first medical monitoring rule, a set of biometric data from the at least first biometric sensor, and transmitting the set of biometric data from the mobile device to a remote processing system for processing a request for insurance.

27 Claims, 11 Drawing Sheets

INSURANCE PROCESSING SYSTEMS AND METHODS USING MOBILE DEVICES FOR MEDICAL MONITORING

CROSS REFERENCE TO RELATED APPLICATIONS

The present application is based on, and claims benefit and priority of, U.S. Provisional Patent Application Ser. No. 61/291,501 filed on Dec. 31, 2009, the contents of which are incorporated herein by reference in their entirety for all purposes. The present application is related to U.S. patent application Ser. No. 12/754,189, filed on Apr. 5, 2010, the contents of which are incorporated herein in their entirety for all purposes.

FIELD

Embodiments relate to insurance processing systems and methods. More particularly, embodiments relate to the collection and use of medical information for insurance processing using mobile devices.

BACKGROUND

The underwriting, issuance and processing of many insurance policies depend on information associated with an individual's health status. For example, long term disability insurance policies generally require that an applicant for insurance provide information about their current health status. This information is often obtained thru diagnostic testing and examinations. Disability insurers use this information to assess the applicant's health status, and to price a policy premium associated with a desired coverage for the applicant.

Other types of insurance may (where permitted by law) collect other health status-related information in the pricing, underwriting, and management of insurance policies. It would be desirable to allow the ready and simple collection of accurate health status information directly from individuals seeking insurance coverage.

Some insurance and other benefits providers promote the wellness of participating individuals by providing reduced premiums, discounts and other incentives. For example, an insurer may provide a discount to individuals who take steps to reduce their blood pressure, or reduce their risk of diabetes by adopting healthier diets or exercising more frequently. It would be desirable to provide simple and accurate ways to encourage such behavior as well as to monitor the adoption of such behavior.

It would further be desirable to provide systems and methods which allow medical and health related data to be collected by an individual and transmitted to insurers and other benefits providers for use in pricing, underwriting and managing insurance and benefits policies.

DETAILED DESCRIPTION

Figure 1:
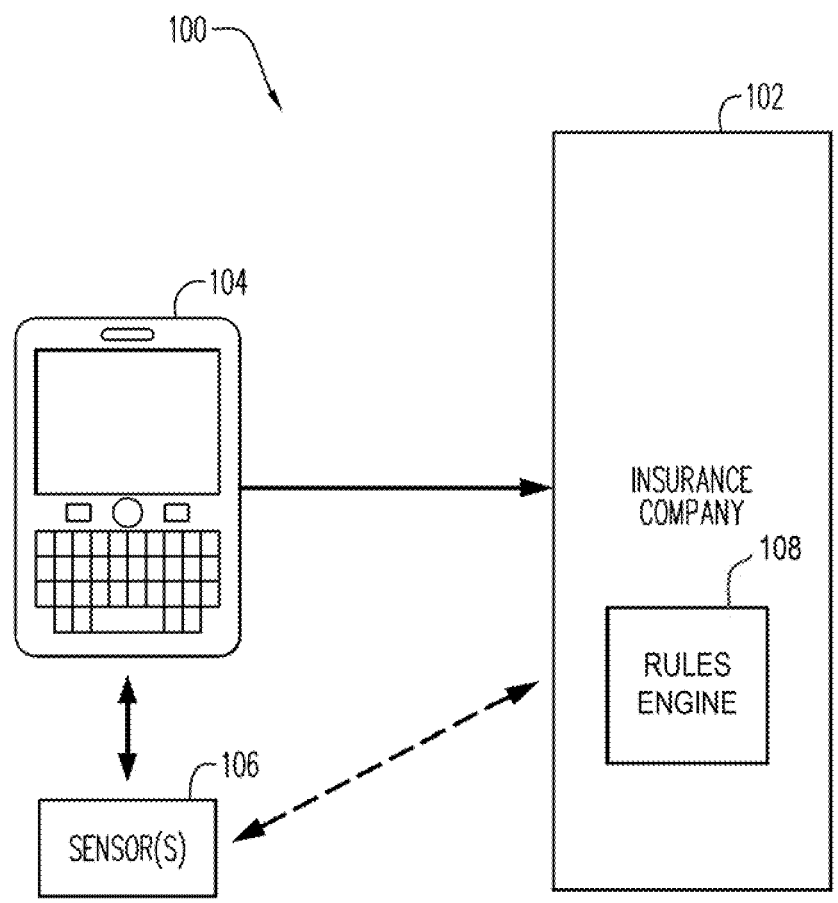
FIG. 1 illustrates a system architecture within which some embodiments may be implemented.

Embodiments of the present invention relate to systems and methods for collecting and utilizing medical and health status information for insurance processing. Embodiments provide applications and mobile devices to allow the ready, convenient and accurate collection and monitoring of medical and health status information from individuals seeking or having insurance coverage, so that such coverage can be priced, managed and underwritten more accurately. As used herein, the term "pricing" generally refers to the calculation of a premium associated with an insurance policy.

In some embodiments, mobile devices, such as smart phones, tablet computers, or other portable communication and computing devices, are provided with software (referred to herein as "applications," "mobile applications" or "medical monitoring applications") that allow users to easily collect, transmit and otherwise provide medical and health status information to insurers and other entities. For example, in some embodiments, users are able to collect and provide biometric data associated with a medical condition or issue so that the user may qualify for insurance coverage or for reduced rates. The mobile applications, in some embodiments, allow users to automatically (or substantially automatically) collect and transmit such data without need to visit a doctor or to use complicated diagnostic equipment. In some embodiments, the mobile applications further allow the efficient and accurate tracking and reporting of a user's health condition, allowing for improved pricing and analysis of insurance policies. Further, the data collected and provided using the mobile applications of the present invention may be used to treat, diagnose and otherwise monitor a user's health status. In some embodiments, different types of data are collected based on the type of risk to be insured or analyzed.

The result is a system and method which provides improved information that may be used to improve the data available to insurers for use in pricing, underwriting and administering insurance policies. The data may further be used by health care providers for use in managing, monitoring and treating a user. In some embodiments, users may be provided with feedback, instructions, and other guidance associated with the maintenance or improvement of their health status based on the information collected and analyzed using embodiments of the present invention.

Pursuant to some embodiments of the present invention, users who provide medical data using features of the present invention may be entitled to improved premiums or may qualify for different levels or types of insurance coverage. For example, pursuant to some embodiments, different risk categories may be specified for different types of insured risks. For simplicity and ease of exposition, embodiments will be described herein by reference to an illustrative example in which a hypothetical insurer uses three levels of risk categories: a "super preferred" risk category, a "preferred risk" category, and a "standard risk" category (where the "super preferred" risk category has preferred pricing and benefits and is available in situations where an insured poses a low risk of loss, and the other two categories have lower qualification requirements). Those skilled in the art, upon reading this disclosure, will appreciate that other variations or types of risk categories may be used in conjunction with embodiments of the present invention (e.g., fewer categories may be used, more categories may be used, etc.). As used herein, each risk category has an associated "threshold value" or minimum requirements to qualify for the pricing or benefits associated with coverage in that risk category.

In some embodiments, a user may be part of a group (e.g., such as an employee of a company having a group benefit plan, or a member of an affinity or other group, such as a weight loss group, or a group of individuals having shared health concerns, etc.) and may provide medical monitoring or health status related information that is analyzed in the aggregate (e.g., at the group level) in order to determine the group's qualification for a particular risk category or to determine the group's qualification for other benefits (e.g., such as discounts or other incentives).

Features of some embodiments will now be described by reference to FIG. 1, which is a block diagram of an insurance processing system 100 pursuant to some embodiments. As shown in FIG. 1, a system 100 includes a mobile device 104 in communication with an insurance company 102. The mobile device 104 is coupled to receive data and information from one or more sensor(s) 106. In some embodiments, as will be discussed further below, data collected by the sensor(s) 106 may be provided to the insurance company 102 via other communication means other than through the mobile device 104. The insurance company 102 operates systems to process insurance policies based on the data received from the mobile device 104, including a medical monitoring rules engine 108. The medical monitoring rules engine 108 may be part of an underwriting or other decisioning system operated by or on behalf of the insurance company 102 and may be used to price, issue, and otherwise administer insurance policies that are based, at least in part, on medical information associated with insureds.

The mobile device 104 may be any of a number of different types of mobile devices that allow for wireless communication and that may be carried with or by a user. For example, in some embodiments, mobile device 104 is a smart phone such as an iPhone®, a mobile device operating the Android® operating system, or other portable computing device having an ability to communicate wirelessly with a remote entity (such as insurance company 102) and with one or more sensor device(s) 106.

Figure 5:
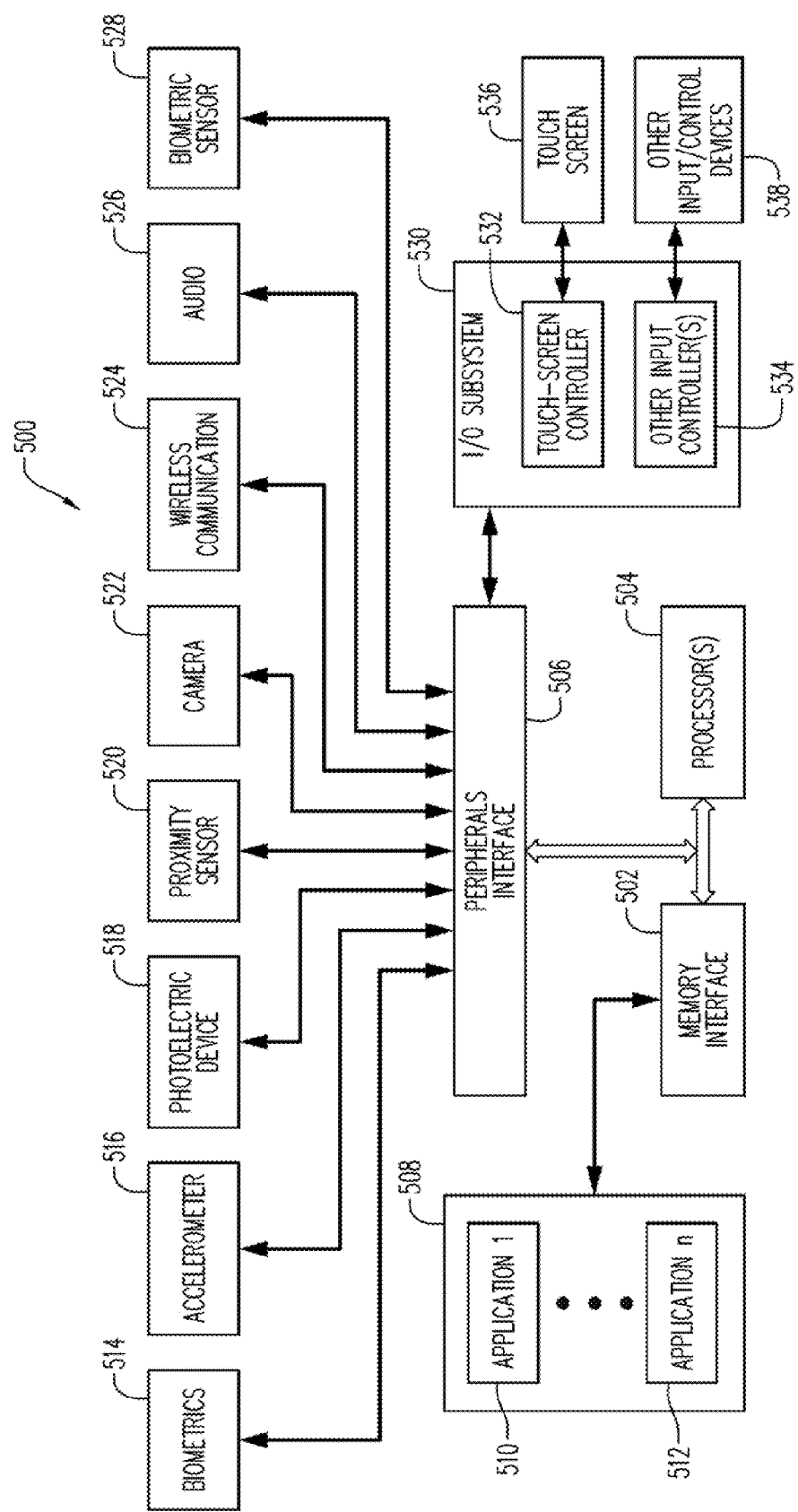
FIG. 5 is a partial functional block diagram of a mobile device and system provided in accordance with some embodiments.

Features of mobile devices 104 will be described further below in conjunction with FIGS. 5 and 6. Preferably, in some embodiments, mobile device 104 is capable of communicating with remote systems (such as insurance company 102) via wireless communication techniques (as will be described further below in conjunction with FIG. 2), and is further capable of communicating with one or more biometric sensors 106, such as heart rate monitors, blood pressure sensors, blood glucose monitors, pulse oximetry sensors, EKG sensors, holter monitors, tamper-proof or tamper-resistant devices (such as treadmills, scales, etc.) or the like. In some embodiments, a sensor 106 may itself be capable of communication with remote devices or entities (such as insurance company 102) to provide health-status related data associated with a user. Mobile device 104 may communicate with a sensor 106 via wired or wireless communication. For example, some sensors 106 may be coupled to mobile device 104 via a USB cable, a headphone cable, or other wired coupling techniques. Other sensors 106 may be coupled to mobile device 104 via Bluetooth®, WiFi or other wireless communication techniques. Examples of a variety of different sensors and sensor configurations are shown and discussed below in conjunction with FIGS. 7A-7C.

Pursuant to some embodiments, the data collected and subsequently transmitted from the mobile device 104 to insurance company 102 may be formatted pursuant to one or more standards to ensure portability and compatibility with other systems and tools. For example, in some embodiments, the data is transmitted using Health Level 7 (or "HL7") messaging formats. In some embodiments, the data is collected and transmitted pursuant to any relevant privacy laws, including, for example the Health Insurance Portability and Accountability Act (or "HIPPA").

The data collected by sensor(s) 106 may be stored temporarily (or for longer periods of time, if appropriate) in a memory of the mobile device 104, or it may be forwarded through the mobile device 104 to insurance company 102 for analysis and processing. In general, the mobile device 104, under control of one or more applications configured pursuant to the present invention, operates to identify the user, identify the time of data collection, identify (if appropriate) the location of data collection, and manage the collection and transmission of data for further use by insurance company 102 or agents of the insurance company 102.

Pursuant to some embodiments, operation of the mobile device 104 for the collection and transmission of medical or health status related data is controlled by one or more mobile applications stored in a memory of the mobile device 104. In some embodiments, the mobile application may allow a user of the mobile device 104 to initiate and (at least to some extent) control the collection of the data. In some embodiments the mobile application provides reports, user interfaces, graphics and other information to the user about the data. The insurance company 102 (or other remote entity or systems) may also provide health-status related feedback to a user. For example, in some embodiments, a remote entity may provide personalized messages, feedback, information or advice to help the user maintain, improve, or control a health condition. As a specific illustrative example, a user who has heart problems and who provides periodic cardiovascular condition data to an insurer (either as a policy-related obligation or on a voluntary basis) may receive specific feedback or messaging in response to the data, such as a supportive message confirming that the user's heart condition is being maintained properly, or as specific advice or information about how to achieve more desirable results. In some embodiments, the user may be incentivized or motivated to learn more about maintaining or improving a particular health condition. For example, a user with a heart condition may be required to read, view or interact with educational information related to their condition (such as a series of videos or articles providing tips on exercise or diet that can reduce cholesterol). The information may be presented to the user via the mobile device 102 under control of a mobile application which records whether the user has viewed or interacted with the educational information.

In some embodiments, the mobile application includes functionality to verify or authenticate the identity of the user so that the insurance company 102 can verify that the data was collected from the correct user. A number of different verification and authentication methods may be used in conjunction with embodiments of the present invention. Different verification and authentication methods may be selected for use in conjunction with different medical monitoring applications based on the level of certainty needed. The methods may range from simple (e.g., in situations where an insurance company is simply providing a discount to a user based on their voluntary provision of health status related data), to advanced (e.g., in situations where an insurance company is attempting to underwrite a policy for a potentially high risk applicant). A mobile application which uses a simple verification method may include password or personal identification number verification for the user to launch the application. A mobile application which uses an advanced verification method may require that the user provide identifying biometric data while health-status related data is being collected. That is, in some embodiments requiring a high degree of certainty that the data is being collected from the correct individual, two sets of data may be collected—data used to identify the user, as well as medical data for use in evaluating or pricing an insurance policy.

As a specific example of this type of verification, a user may be required to authenticate or verify his identity by connecting one sensor to provide electrocardiogram (ECG) data (which may then be compared to a stored pattern to determine if the user being monitored is the correct user). An illustrative example configuration of such a system is shown in FIG. 7B. An ECG is a signal that measures the change in the electrical potential of the heart muscle over time. The trace of a heartbeat in the ECG produces three complexes: P, QRS, and T. The differences of chemical/potential changes that happen among the heart cells, called myocytes, cause these various waveforms in the ECG. Since there are differences in physical characteristics of the heart and of different people, the ECG's of different people are unique. Therefore they can be used as signatures of identities. As a result, in one specific embodiment, a user whose identity must be verified while health-status data is being collected, may operate a mobile device 104 having two sensors 106 coupled thereto: (1) an EKG sensor (used to verify the user's identity during a data collection process), and (2) a sensor used to collected the desired health-status data (e.g., such as a blood pressure monitor or the like). The two sensors may be coupled to the mobile device 104 through one or more interfaces, allowing simultaneous operation of the sensors. Those skilled in the art will appreciate that a number of different verification methods and sensor devices may be used in conjunction with embodiments of the present invention, for example, verification may be performed using finger vein sensing, DNA testing, fingerprinting, retinal scans, facial recognition or the like.

As another example of an advanced level of verification (which may be used in situations where the insurer needs to verify the user's identity with a high degree of certainty), a monitoring bracelet or other wearable device may be required. In some embodiments, the monitoring device may be a sensor 106 which is in communication with the mobile device 104 and which must be worn during a monitoring period. For example, the monitoring device may be installed or placed on the user by a certified agent of the insurance company, and communication between the monitoring device and the mobile device 104 is verified. Then, when the user is scheduled or prompted to perform a medical data monitoring process pursuant to the present invention, a communication session is initiated between the monitoring device and the mobile device 104 to confirm that the monitoring device is proximate the mobile device 104 during the period of data collection. In this manner, a high level of certainty that the user operating the mobile device 104 during medical data collection processing is the correct user. In other embodiments, video or audio capabilities of the mobile device 104 may be used to further verify the identity of the user operating the device.

Embodiments of the present invention utilize such identity information to verify that a user being monitored for certain medical information is the correct user. Once the user's identity has been verified (or while the user's identity is being verified), a second sensor may be operated to obtain other medical or health status related data for transmission to the insurance company. In this manner, embodiments allow the collection of data from a user with a high degree of certainty that the data was collected from the right person. Other verification techniques may also be utilized, including, for example, fingerprint or other biometric techniques.

The insurance company 102 may use the collected health status data to determine a user's eligibility for a particular policy or premium level, to provide discounts or benefits to existing insured individuals, and to otherwise underwrite, manage or administer policies and benefits that require accurate and current medical information. The use of such data in adjusting existing policies will be described further below in conjunction with FIG. 8, and the use of such data in issuing new policies will be described in conjunction with FIG. 9.

Pursuant to some embodiments, data may be transmitted between devices using a wireless network. In some embodiments, some, or all, of the data may be transmitted using other network communication techniques (e.g., such as satellite communication, RFID, or the like). In some embodiments, some or all of the data transmitted between devices may be encrypted or otherwise secured to prevent intrusion.

Figure 2:
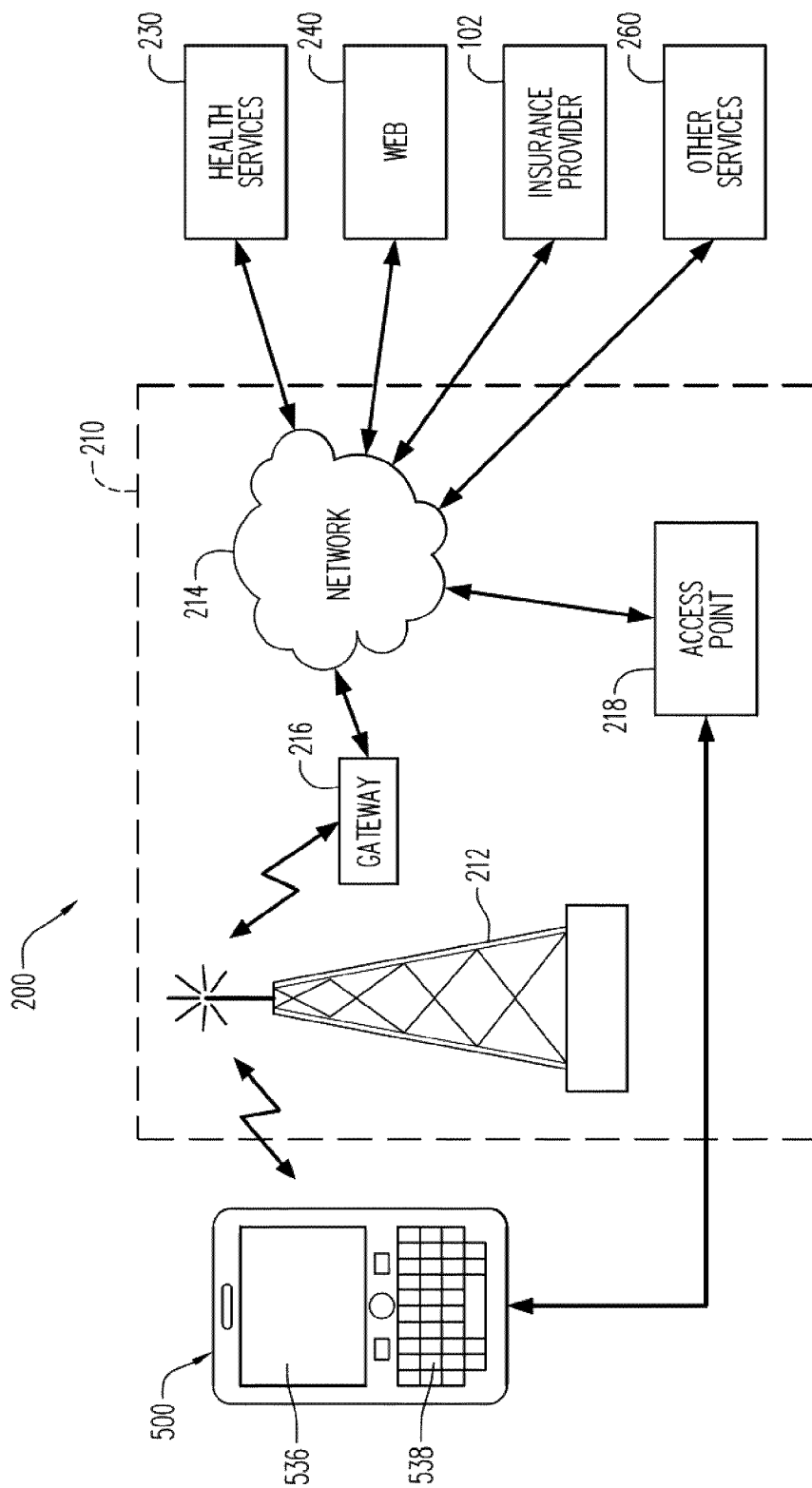
FIG. 2 illustrates a mobile system architecture within which some embodiments may be implemented.

Reference is now made to FIG. 2, which is a block diagram of an example network environment 200 showing communication paths between a mobile device 500 and the insurance provider systems 102 (as well as other devices and data sources). The mobile device 500 may be, for example, a mobile telephone, PDA, personal computer, or the like. For example, the mobile device 500 may be an iPhone® from Apple, Inc., a BlackBerry® from RIM, a mobile phone using the Google Android® operating system, a portable or tablet computer (such as the iPad® from Apple, Inc.), or the like. Pursuant to some embodiments, the mobile device 500 may be coupled to one or more sensor devices to collect identity and health-status related information from a user of the mobile device 500. In general, mobile device 500 may be any mobile computing and/or communications device which is capable of executing the insurance applications described herein.

The mobile device 500 of FIG. 2 can, for example, communicate over one or more wired and/or wireless networks 210. As an example, a wireless network can be a cellular network (represented by a cell transmitter 212). A mobile device 500 may communicate over a cellular or other wireless network and through a gateway 216 may then communicate with a network 214 (e.g., such as the Internet or other public or private network). An access point, such as access point 218 may be provided to facilitate data and other communication access to network 214. The access point 218 may be, for example, compliant with the 802.11g (or other) communication standards.

In some embodiments, mobile device 500 may engage in both voice and data communications over the wireless network 212 via access point 218. For example, the mobile device 500 may be able to place or receive phone calls, send and receive emails, send and receive short message service ("SMS") messages, send and receive email messages, access electronic documents, send and receive streaming media, or the like, over the wireless network through the access point 218. Similar communications may be made via the network 212.

In some embodiments, a mobile device 500 may also establish communication by other means, such as, for example, wired connections with networks, peer-to-peer communication with other devices (e.g., using Bluetooth networking or the like), etc.

The mobile device 500 can, for example, communicate with one or more services over the networks 210, such as service providers 230-260 and the insurance provider systems 102 (described above in conjunction with FIG. 1 and further below in conjunction with FIG. 3). For example, the mobile device 500 may communicate with one or more health services providers 230 (e.g., such as a doctor, medical provider, testing company, laboratory, or the like) to send or receive data associated with a user's health information. As another example, the mobile device 500 may communicate with one or more web services 240 to receive or transmit data (e.g., such as mapping services to identify the location of a testing lab, a pharmacy, or the like). The mobile device may also be in communication with a number of other service providers 260.

The mobile device 500 can also access other data over the one or more wired and/or wireless networks 210. For example, content providers, such as news sites, RSS feeds, web sites, blogs, social networking sites, developer networks, etc., can be accessed by the mobile device 500. Such access can be provided by invocation of a web browsing function or application (e.g., a browser) in response to a user launching a Web browser application installed on the mobile device 500.

For example, in some embodiments described herein, the mobile device 500 may interact with insurance provider system 102 to receive data associated with a mobile application from the insurance provider. For example, the insurance provider may require the user to install and interact with the mobile application in order to confirm that the user is eligible for insurance coverage or that the user is eligible for a discount or other benefit. The mobile application, once installed on the mobile device 500, may include a number of instructions for the user, including instructions regarding the specific sensor configuration and the frequency and duration of health-related status data to collect. In some embodiments, the mobile application may also provide related information to the user, including, for example, health tips and suggestions for the user to improve, monitor or maintain a medical status. Such information may be provided by one or more web services 240 or health services 230 and aggregated and displayed to the user via the mobile application on the mobile device 500.

In use, when collecting health status-related data from a user, the mobile device 500 may receive the data from one or more sensors coupled to the mobile device 500. The health status-related data may then be transmitted over networks 210 to the insurance provider 102 and/or to one or more health services 230 for analysis. In some embodiments, the insurance provider 102 may utilize the received data in order to make an underwriting or pricing determination associated with an insurance policy associated with the user.

A number of policy underwriting algorithms or approaches maybe used to incorporate the health status-related data into a premium determination. The health status related data may be used in decisions related to new policies as well as for renewal policies. The data may further be used to encourage or promote improved health habits or conditions which result in fewer claims or health problems. A number of illustrative (but not limiting) algorithms and threshold criteria for a variety of health status related information used in underwriting various risk types are shown below in Table I. In Table I, the "risk types" shown include "L" (Life), "WC" (Workers Compensation), "GDB" (Guaranteed Death Benefits), and "A" (Auto).

TABLE I

| Health Data Type | Risk Type | Super Preferred Risk Threshold | Preferred Risk Threshold | Standard Risk Threshold |
|---|---|---|---|---|
| Blood pressure ("BP") History | L, WC, GDB | No blood treatment medications detected | No blood treatment medications detected | BP controlled by medications |
| Blood pressure ("BP") readings | L, WC, GDB | BP <140/85 if age <=60 or BP <150/90 if age >=61 | BP <140/90 if age <=60 or BP <150/90 if age >=61 | Average BP reading over 2 year period <=155/95 if age <=60 or average BP reading over 2 year period <=160/95 if age >=61 |
| Nicotine Readings | L, WC, GDB | No nicotine use detected during 5 year testing period | No nicotine use detected during 3 year testing period. | No nicotine use detected during 1 year testing period. |
| Cholesterol Levels | L, WC, GDB | 210-240 (depending on rest of health history) | 250-270 (depending on rest of health history) | <300 |
| Cholesterol (HDL) Levels | L, WC, GDB | <=5.0 | <=6.0 | <=8.0 |
| Alcohol Use | L, WC, A | Blood Alcohol Content ("BAC") is not >0.08% more than 10x/year | BAC is not >0.08% more than 30x/year | BAC is not >0.08% more than 40x/year |
| Substance Abuse | L, WC, A | No illegal drug usage detected for 10 year testing period | No illegal drug usage detected for 7 year testing period | No illegal drug usage detected for 3 year testing period |
| Weight | L, GDB, A | Weight <=162 pounds if 5' 4" male, or <=140 | Weight <=180 pounds if 5'4" male . . . | Weight <=209 pounds if 5'4" male . . . |

TABLE I-continued

| Health Data Type | Risk Type | Super Preferred Risk Threshold | Preferred Risk Threshold | Standard Risk Threshold |
|---|---|---|---|---|
| | | pounds if 5'4" female . . . | | |
| Cardiovascular | L, WC | EKG testing shows no cardiac issues | EKG testing shows minor cardiac issues | EKG testing shows minor cardiac issues |
| Fitness test (stress test) | L, WC, GDB, A | Testing shows metabolic equivalent unit ("METs") >=15 | Testing shows METS >=10 | Testing shows METS <10 |
| Workplace Safety - Lifting Behavior | L, WC, GDB | Testing shows excellent lifting behavior | Testing shows above average lifting behavior | Testing shows average lifting behavior |
| Driving Behavior | A | Monitoring shows excellent behavior over 30 day testing period | Monitoring shows above average behavior over 30 day testing period | Monitoring shows average behavior over 30 day testing period |

The mobile device 500 can perform a number of different device functions which can be controlled or specified by the insurance company by providing instructions, data or commands to the mobile device 500. The instructions, data or commands may be executed by a processor of the mobile device 500 causing the mobile device 500 to be, effectively, under control of the insurance company allowing the insurance company to control the collection of medical data from a user. The mobile device 500 may operate as a telephone, an email device, a network communication device, a media player device, etc., under control of one or more applications installed on the mobile device 500. In some embodiments, a user operating the mobile device 500 may interact with the applications using a keypad 538 which may be a tactile keypad with individual keys, or which may be a touch screen keypad. The user is presented with information and graphics on a display screen 536. For example, a user who is operating a mobile application pursuant to the present invention may be presented with a series of user interfaces which may: (1) instruct the user on the configuration and use of one or more sensors, (2) instruct the user regarding the frequency and duration of data collection required, (3) instruct the user regarding any identity or authentication processes required, and (4) present the user with summary or detailed reports of the health status-related data collected by the sensors. In some embodiments, tips and other health related information may be provided to the user based on the type of health status-related data being collected (e.g., if the user is diabetic, and the health status-related data being collected includes blood sugar data, tips may be presented to the user to help the user manage their condition). Further details of the collection and use of such health status-related data will be provided further below.

Figure 3:
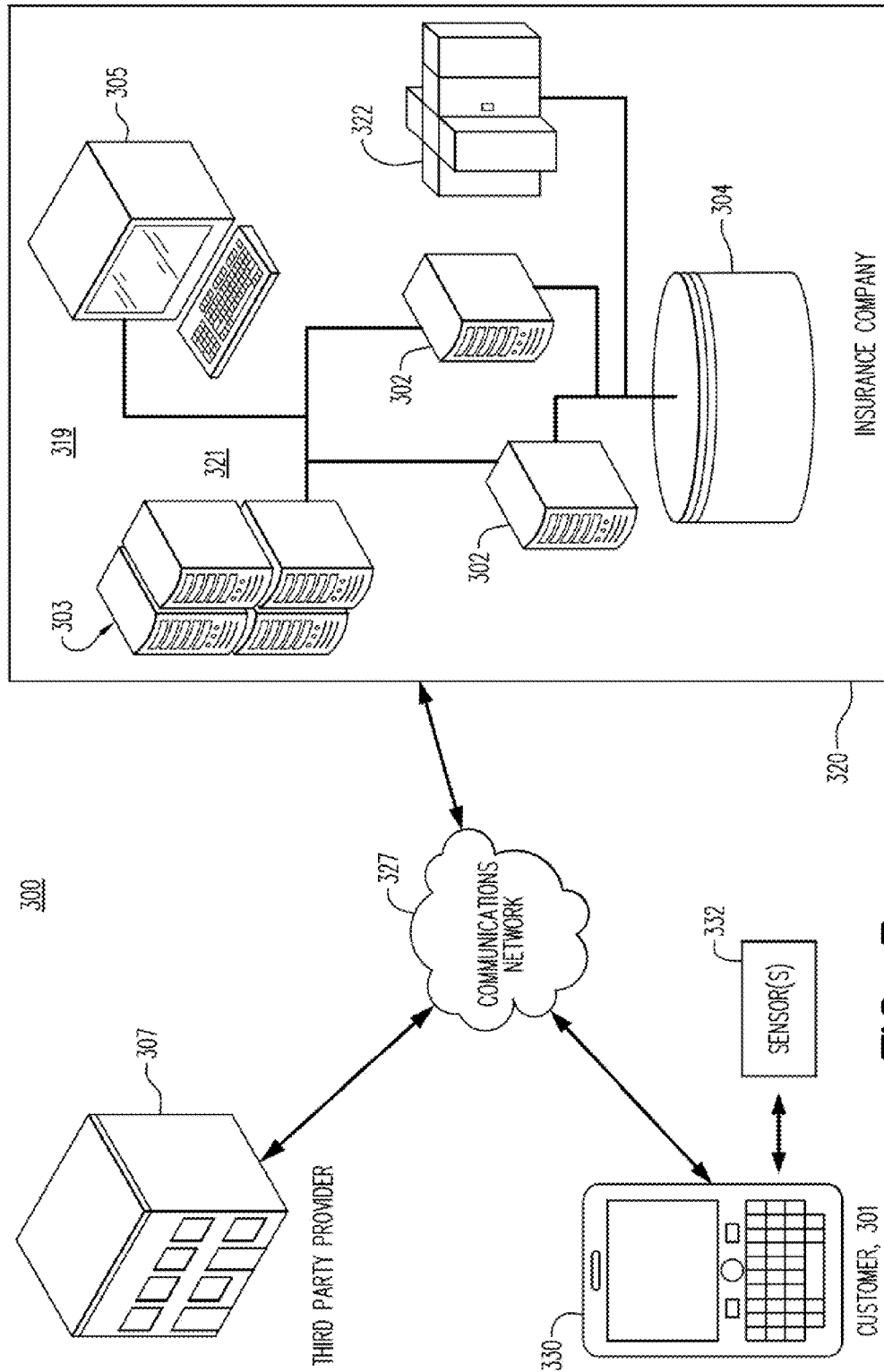
FIG. 3 is a block diagram of an insurance system pursuant to some embodiments.

Reference is now made to FIG. 3 which is a schematic diagram of a system 300 for monitoring, evaluating, and providing feedback on insurance, such as insurance related to, or whose pricing is depending at least in part on, an applicant's health. In FIG. 3, insurance company 320 provides customer 301 with insurance coverage. The type of insurance provided by insurance company 320 may be any type of insurance, such as general liability insurance, although the present invention is described primarily in terms of medical or health-related insurance. Insurance company 320 can simultaneously provide services to multiple customers, although only one customer 301 is shown in FIG. 3 for clarity.

Mobile device 330, pursuant to some embodiments, stores an application program that may be loaded onto the mobile device 330 from an insurance company 320 or from an application repository (e.g., such as Apple's App Store or the like). The application, when launched, prompts the customer 301 for information used to interact with the insurance company 320 or to collect and provide health-status related information to the insurance company 320. A variety of different types of data and information may be provided from mobile device 330 to insurance company 320, including static data regarding the customer 301, such as the customer's name, address, contact information, age, height, weight, policy information, etc. Other variable information may be provided (as described in each of the mobile application embodiments described above). Dynamic or collected data may also be provided by collecting data from one or more sensor(s) 332 in communication with the mobile device 330. For example, the data collected by sensor(s) 332 may be aggregated and then transmitted to the insurance company 320 for analysis. In some embodiments, the data collected by sensor(s) 332 may be immediately transmitted from the mobile device 330 to the insurance company 320 (e.g., using the mobile device 330 as a forwarding device so that sensitive medical or health related data need not be stored in the mobile device 330) for evaluation and processing. In some embodiments, some or all of the collected data may be also (or alternatively) be transmitted from the mobile device 330 to one or more third party providers 307 (e.g., such as medical or health specialists).

Insurance company 320 has a computer system 319 that includes application servers 302, load balancing proxy servers 303, data storage unit 304, business logic computer 322, and user interface module 305 to perform risk evaluation and underwriting based on the collected health status-related data. Employees of the insurance company 320 and other authorized personnel use user interface module 305 to access the insurance company computer system. User interface module 305 may be any type of computing device that is configured to communicate with other computer systems. User interface module 305 may be connected directly to application server 302, or may access an application server 302 via the load balancing proxy servers 303. User interface module 305 may connect to load balancing proxy servers 303 via a local area network, a private data link, or via the internet.

Although depicted as being part of insurance company 320 in FIG. 3, user interface module 305 may be located remotely. The business logic computer 322 is connected to the data storage unit 304 and application servers 302 over a local area network 321, which may be part of communication system 327. In addition, other network infrastructure, including, for example a firewall, backup servers, and back up data stores, may also be included in the system 319, without departing from the scope of the invention. Communications over the local area network 321 and/or over the Internet, in one implementation, may be encrypted. In addition, such communications, whether encrypted or not, may also be digitally signed for authenticating the source of the communications. The computer system 319 may also include a certificate authority to authenticate one or more of the communications using public key infrastructure.

Based on health status-related data collected from the mobile device 330 and any third party data sources, an evaluation module analyzes and evaluates data associated with a customer 301. As used herein, a "module" may be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

As used herein, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. In addition, entire modules, or portions thereof, may also be implemented in programmable hardware devices such as field programmable gate arrays, programmable array logic, programmable logic devices or the like or as hardwired integrated circuits.

A number of different business logic modules may be operated by insurance company 320 to process data collected by mobile devices 330. For example, an underwriting module may be implemented, for example, in business logic computer 322, and used to underwrite or alter insurance pricing for customer 301 based on the received health status-related data. The business logic module may use predictive models, such as neural networks, Bayesian networks, and support vector machines, in performing the underwriting and premium adjustment. In one embodiment, the premium of an insurance policy is increased or decreased if health status-related data received from customer 301 warrants. For example, in a situation where the customer 301 has agreed to provide health status-related data on a regular basis to demonstrate that a health condition is under control (e.g., such as diabetes or other medical conditions which may be controlled using diet, medication or the like), the health status-related data may be used by computer 322 to determine if the customer 301 has successfully met conditions to receive a discount or reduced premium based on the management of the health condition. Instead of altering premium rates, other terms of the insurance policy can be altered, such as the policy deductible.

In some embodiments, a number of different risk tiers may be enforced using data collected pursuant to the present invention, such as the risk tiers described above in conjunction with Table I. A business logic module (e.g., implemented in business logic computer 322) may be used to analyze the data received from mobile devices 330 and to determine if a customer 301 qualifies for the pricing or terms associated with a particular tier based on threshold data and rules associated with the policy type and the insured risk. The rules and threshold data may be stored at, for example, the data storage device 304. In some embodiments, the business logic module may also apply one or more business process rules associated with a particular coverage or data collection event. For example, for policies that are structured in a "pay as you go" coverage type, a business rule associated with the policy may specify that when health status related data is received from a mobile device 330 for a given customer 301 that the received data may result in a change to the risk category immediately. For other policies, the business rule may specify that health status related data may result in a risk category change upon the next renewal date (or issuance) of a policy. The business rules may further specify items such as the frequency of data collection for a given type of data or for a particular customer, as well as response data to be transmitted to a mobile device 330 in response to a data collection event.

In another scenario, insurance company 320 awards customer 301 with premium discounts, or other advantageous rewards, simply for agreeing to use (and, in some embodiments, actually using) the mobile applications as described above. Insurance company 320 may award different discounts depending on the nature and amount of data provided by customer.

In one implementation, software operating on the application servers 302 act merely as presentation and data extraction and conversion servers. All substantive business logic, including underwriting and pricing determinations, is carried out on the business logic computer 322. In this implementation, the application servers 302 obtain data from the data storage unit 304 and the business logic computer 322 and incorporate that data into web pages (or other graphical user interface formats). These web pages are then communicated by the application servers 302 through the load balancing proxy servers 303 to user interface module 305 for presentation. Upon receiving input from user interface module 305, the application server 302 translates the input into a form suitable for processing by the business logic computer 322 and for storage by the data storage unit 304. In this implementation, the application servers can be operated by third parties, who can add their own branding to the web pages or add other customized presentation data. Alternatively or in addition, at least some of the business logic is also carried out by the application servers 302.

In some embodiments, the application servers 302 are software modules operating on one or more computers. One of the computers on which the application servers 302 are operating may also serve as the business logic computer 322 and/or as a load balancing proxy server 303.

In some embodiments, the software operating on user interface module 305 includes a thin or thick client application in addition to, or instead of a web browser. The thin or thick client application interfaces with a corresponding server application operating on the application server 302.

Figure 4:
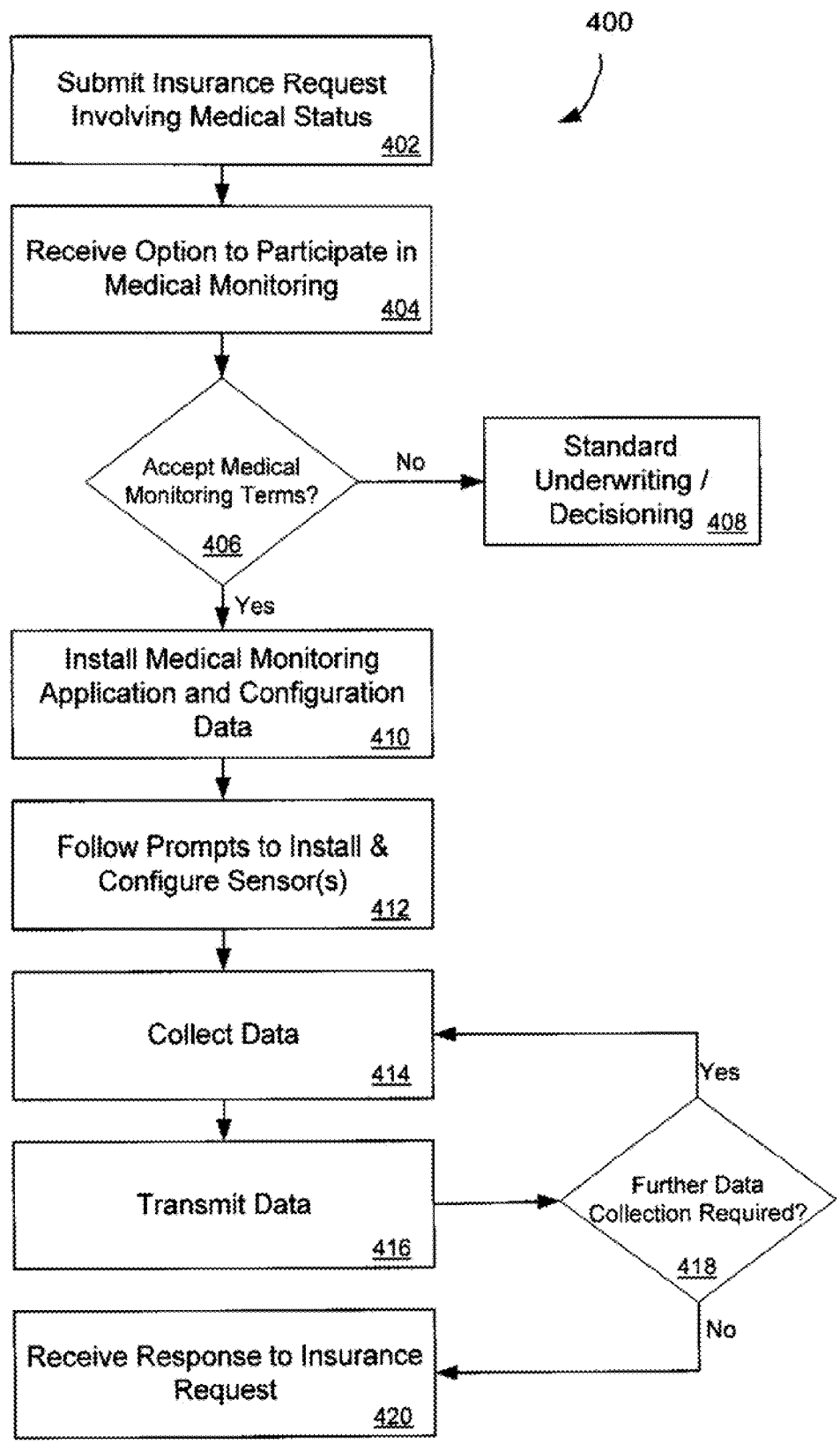
FIG. 4 is a flow diagram depicting a process pursuant to some embodiments.

Reference is now made to FIG. 4 which is a flow diagram depicting a process 400 for installing and operating a medical monitoring application pursuant to some embodiments. Some or all of the steps of process 400 may be performed using a mobile device such as the mobile device 104 of FIG. 1 (or the mobile device 500 described in further detail below in conjunction with FIGS. 5 and 6). As shown, processing begins at 402 where a user submits an insurance request which involves some medical status. For example, the insurance request may be a request for new or updated insurance coverage of a risk that has a component that is related to or based on health or medical information, such as a request for life insurance, workers compensation insurance, a guaranteed defined benefit policy, or automobile insurance. The request submitted at 402 may be a request for insurance coverage in which the user indicates the existence of a medical condition which could have an impact on the underwriting analysis or pricing of the policy. For example, the request may be for a life insurance policy for an individual who has indicated a family (or personal) history of heart disease, or a request for an automobile policy for an individual who has had a driving under the influence conviction in the past (or for other health issues that are discussed herein, including the issues identified in Table I, above).

The information provided at 402 is provided to an insurance company (such as insurance company 320 of FIG. 3) for initial processing. The insurance company may determine that medical monitoring is an appropriate part of the underwriting or policy analysis process for the individual (e.g., based on the application of one or more business rules by business logic computer 322 of insurance company 320) and respond to the request (at 404) with an option for the individual to participate in medical monitoring pursuant to the present invention. The response at 404 may provide detailed information to the individual regarding the scope and nature of the medical monitoring, including the frequency and nature of monitoring, as well as the advantages of participating in the medical monitoring. For example, the individual may be offered an ability to qualify for reduced premiums, discounts, or expedited underwriting on the application if the individual participates in the medical monitoring.

At 406 the individual either accepts or declines the medical monitoring terms. If the individual declines, processing may continue at 408 where the insurance request received at 402 is processed using a standard underwriting and decisioning process (e.g., one which may require that the individual submit to testing at a clinic or by a paramedic, or which may not allow the individual to qualify for reduced premiums or discounts). If the individual accepts the medical monitoring terms, processing continues at 410 where the individual is instructed to install a medical monitoring application and related configuration data on their mobile device. For example, the user may be instructed to download and install a medical monitoring application on a mobile device. The medical monitoring application may be installed from the mobile device (e.g., by interacting with an application download system), or from a personal computer in communication with the mobile device. The application may be downloaded from the insurance company 320 or from an application marketplace (such as the iTunes® Store or Android® Store).

Processing continues at 412 where the medical monitoring application is launched (e.g., by interacting with an icon associated with an executable file installed on the mobile device) and prompts the user to install and configure one or more sensors in order to collect data for use by the medical monitoring application. For example, when the medical monitoring application is launched by a user, the application may walk the user through a series of user interfaces to perform configuration process which may include installing or configuring one or more sensor devices for use with the application. Each medical monitoring application may have different or specific configuration instructions depending on the nature of the medical or health status-related data that is to be collected. For example, a medical monitoring application that is designed to collect data associated with a diabetic user may provide instructions for installing and configuring a blood glucose sensor. A medical monitoring application that is designed to collect data associated with a user's blood pressure may provide instructions for installing and configuring a blood pressure sensor. The sensor(s) to be installed and configured at 412 may be provided to the user by the insurance company 320 or the user may be instructed how to obtain the appropriate sensor(s).

In some embodiments, the configuration of sensors may include establishing a baseline reading for the user. The baseline reading may include connecting the sensor, and then guiding the user through an initial configuration process which includes taking one or more measurements to establish initial values for the medical or health status-related data. In some embodiments, the configuration results and initial data may be transmitted to the insurance company 320 or to a medical professional for verification. In some embodiments, where a high level of confidence that the user's identity is known during the collection of data, processing at 412 may further include installing and configuring one or more sensors used to collect verification data. As an example, in embodiments where the verification of a user's identity is performed using EKG readings, processing at 412 may include prompting the user to install and configure an EKG sensor as well as to take initial baseline EKG readings using the EKG sensor. The baseline EKG readings may then be transmitted to the insurance company 320 to establish a "fingerprint" or comparison file for use in later identifying or authenticating the identity of a user during the collection of medical or health status-related data. Processing at 412 may also include collecting location and other data from the mobile device for use in identifying a user or operator of the mobile device during data collection.

Once the sensor(s) have been installed and configured, and the medical monitoring application has successfully registered with the insurance company 320, processing continues at 414 where the application is used (in conjunction with the sensor(s)) to collect the relevant medical or health status-related data. In some embodiments, the timing and frequency of the collection of data is controlled by configuration data associated with the mobile application (or instructions received by the mobile application from the insurance company 320). For example, some medical monitoring applications may require that data be collected on a daily schedule, at a particular time of day (e.g., first thing in the morning, etc.). In such embodiments, the mobile application may trigger an alarm or calendar reminder prompting the user to remember to collect the data by connecting the required sensor(s) to the mobile device and attaching the sensor(s) to take the required measurements. As a specific example, in the case of a diabetic user who is using the medical monitoring application to monitor his or her blood sugar levels, processing at 414 may include triggering an alarm or calendar reminder on the mobile device on a daily basis, and then prompting the user to connect a blood sugar monitor to their body and to the mobile device. Processing at 414 may also include diagnostic routines to ensure that the sensor(s) have been properly attached and configured. Once the sensor(s) are operational, processing continues as the data from the sensor(s) is received by the mobile device. In some embodiments, where a data identifying or authenticating the identity of the user is required, processing at 414 may also include the collection of such authentication data.

Processing continues at 416 where the collected data is packaged and transmitted to the insurance company 320 for further analysis. In some embodiments, some or all of the collected data may also be displayed to the user to provide the user with feedback on the status of their health or medical condition. In the case of a user who is a diabetic, for example, a current blood sugar reading may be displayed on a display device of the mobile device as well as a historical summary or chart of the previous readings taken by the sensor. In this manner, users are able to both provide current and accurate health status-related data to their insurer as well as view their own progress or status. In some embodiments, the presentation of such data may be enhanced or appended with recommendations or tips from medical experts or health professionals to allow the user to improve or control their condition. The user may be required to read, view or interact with such recommendations or tips in order to qualify for certain premiums or incentives.

In embodiments where data is also collected regarding the identity of the user, the identity or authentication data is also transmitted to the insurance system to allow the insurance system to confirm that the collected health status-related data is associated with the correct user. In some embodiments, data collected at 414 is temporarily stored in the mobile device and is forwarded to the insurance company 320 for processing. A subset of the data is stored in the mobile device for reporting or feedback to the user.

Processing may continue at 418 where a determination is made whether further data collection is required. For example, processing at 418 may include receipt (by the mobile application) of a response message from the insurance company 320 indicating whether additional data is to be collected. The response message may specify details of the next data collection event (such as, for example, the timing or frequency of the subsequent data collection, as well as instructions for the configuration and use of the sensors for such subsequent data collection). For example, in the case where the user has submitted a request for automobile insurance, and the user has a history of alcohol abuse, the response from the insurance company 320 may instruct the mobile application to prompt the user to take a subsequent blood alcohol test ("BAT") on a randomized schedule. The response message from the insurance company 320, for example, may specify the next time and date on which the user is to be prompted to take the BAT. In this manner, the business rules and logic of the insurance company 320 may control the collection of additional medical or health status related data for use in underwriting or otherwise analyzing insurance requests (such as applications for new or renewal policies).

Pursuant to some embodiments, if further data collection is required, the response message defining the scope and details of the further data collection may be modified based on the prior data received. For example, as more data is collected, the insurance company 320 may increase the sensitivity of the monitoring or modify the nature of the sensor operations to ensure that accurate and relevant medical data is collected by the sensors.

If a determination is made that no further data collection is required, a final response to the insurance request may be received at 420. For example, the response received at 420 may be a final determination from an underwriting business process performed at the insurance company 320 such as a denial of coverage, issuance of coverage, etc.

In this manner, a user may submit requests for insurance that involve some aspect of medical monitoring, and may be able to perform the medical monitoring using one or more sensors in communication with a mobile device. Such medical monitoring allows increased convenience for the user, and may eliminate or reduce the need for the user to visit or schedule time with a medical testing professional. The medical monitoring using a mobile device and sensor may also provide reduced costs for insurers as there is a significant cost for paramedics and medical professionals to perform in-home or other scheduled visits to collect medical information associated with insurance applications. Further, embodiments provide improved collection and accuracy of medical information about users, allowing insurers to more accurately underwrite and process insurance requests. Users enjoy added benefits such as potentially reduced premiums and discounts, as well as access to current and accurate information about their medical condition.

Further details of some embodiments of mobile devices that may be used in conjunction with embodiments of the present invention will now be described by reference to FIGS. 5 and 6. Reference is first made to FIG. 5, where details of a mobile device 500 according to some embodiments is shown. As depicted, the mobile device 500 includes a number of components which may be controlled or perform functions in conjunction with one more application programs 510-512 to perform the features of some embodiments.

The mobile device 500 can include a memory interface 502 one or more data processors, image processors and/or central processing units 504, and a peripherals interface 506. The memory interface 502, the one or more processors 504 and/or the peripherals interface 506 can be separate components or can be integrated in one or more integrated circuits. The various components in the mobile device 500 can be coupled by one or more communication buses or signal lines.

Sensors, devices and subsystems can be coupled to the peripherals interface 506 to facilitate multiple functionalities. For example, one or more sensors, including biometrics sensors 514 and 528, an accelerometer 516, a photoelectric device 516, a proximity sensor 520, a camera 522, a wireless communication unit 524, and an audio unit 526 may be provided to facilitate the collection, use and interaction with data and information and to achieve the functions of the insurance applications described herein.

The mobile device 500 may include one or more input/output (I/O) devices and/or sensor devices. For example, input controllers 534 may be provided with a speaker and a microphone (not shown) to facilitate voice-enabled functionalities, such as phone and voice mail functions. In some implementations, a loud speaker can be included to facilitate hands-free voice functionalities, such as speaker phone functions. An audio jack can also be included for use of headphones and/or a microphone.

The I/O subsystem 530 can include a touch screen controller 532 and/or other input controller(s) 534. The touch-screen controller 532 can be coupled to a touch screen 536. The touch screen 536 and touch screen controller 532 can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the touch screen 536.

The other input controller(s) 534 can be coupled to other input/control devices 538, such as one or more buttons, rocker switches, thumb-wheel, infrared port, USB port, and/or a pointer device such as a stylus. The one or more buttons (not shown) can include an up/down button for volume control of the speaker and/or the microphone. One or more medical sensor(s) (such as biometric sensors, EKG sensors, glucose monitors, blood pressure monitors, or the like) may be coupled to the mobile device through one or more of the peripheral interface 506 (such as sensors 514, 528) and/or through the input controller(s) 534. Sample configurations which show different sensors coupled to a mobile device 500 are shown and discussed below in conjunction with FIG. 7A-C, although those skilled in the art, upon reading this disclosure, will appreciate that a wide variety of different configurations and types of sensors may be used.

In some implementations, a proximity sensor 520 can be included to facilitate the detection of the user positioning the mobile device 500 proximate to the user's ear and, in response, to disengage the touch-screen display 536 to prevent accidental function invocations. In some implementations, the touch-screen display 536 can be turned off to conserve additional power when the mobile device 500 is proximate to the user's ear. In some embodiments, a proximity sensor (such as sensor 520) may be used to identify when a biometric sensor is properly coupled or worn by a user. For example, in some embodiments, a biometric sensor such as a blood pressure cuff or collar may be detected by a proximity sensor 520 while data is collected. If the blood pressure cuff or collar is receiving data but is not proximate or near the mobile device 500, the proximity sensor 520 will provide data to the medical monitoring application indicating the situation and the data may be transmitted along with the collected data to the insurance provider for further analysis.

Other sensors can also be used. For example, in some implementations, a photoelectric device 518 may be provided to facilitate adjusting the brightness of the touch-screen display 538. In some implementations, an accelerometer 516 can be utilized to detect movement of the mobile device 500. In some embodiments, the mobile device 500 may include circuitry and sensors for supporting a location determining capability, such as that provided by the global positioning system (GPS) or other positioning system (e.g., systems using Wi-Fi access points, television signals, cellular grids, Uniform Resource Locators (URLs)). In some implementations, a positioning system (e.g., a GPS receiver) can be integrated into the mobile device 500 or provided as a separate device that can be coupled to the mobile device 500 through a peripherals interface 506 to provide access to location-based services. The positioning and location-based services may be used, for example, to tag data transmitted from the mobile device 500 to insurance provider systems 102. For example, such location data may be used to authenticate the identity of a user who provides medical data. For example, if the user providing medical data (e.g., using the process of FIG. 4) is known to be a resident of Connecticut, a possible fraud or identity warning may be triggered if medical data is collected while an operator of the mobile device is located in California. The position and location-based data can also be used to collect data regarding a user's driving habits, such as speed, location, acceleration, deceleration, etc.

The mobile device 500 can also include a camera lens and sensor 520. In some implementations, the camera lens and sensor 520 can be located on the back surface of the mobile device 500. The camera can capture still images and/or video. The camera may be used, for example, to capture images of a user's sensor setup to facilitate trouble shooting (e.g., by transmitting the images to a customer support specialist associated with the insurance provider 102 or a medical professional) as well as to authenticate the identity of the user when they are providing medical data (e.g., during processing of FIG. 4). For example, a user who is operating the medical monitoring application may be prompted to take a photo of themselves with the sensor(s) installed and attached to their body as proof that the medical or health status-related information was collected from the correct individual. Such image data can further be combined with location and time data to further verify that the collected medical data was collected from the correct user.

The mobile device 500 can also include one or more wireless communication subsystems 524, such as an 802.11b/g communication device, and/or a Bluetooth® communication device. Other communication protocols can also be supported, including other 802.x communication protocols (e.g., WiMax, Wi-Fi), code division multiple access (CDMA), global system for mobile communications (GSM), Enhanced Data GSM Environment (EDGE), 3G (e.g., EV-DO, UMTS, HSDPA), etc.

In some implementations, additional sensors or subsystems may be coupled to the peripherals interface 506 via connectors such as, for example a Universal Serial Bus (USB) port, or a docking port, or some other wired port connection.

The memory interface 502 can be coupled to memory 508. The memory 508 can include high-speed random access memory and/or non-volatile memory, such as one or more magnetic disk storage devices, one or more optical storage devices, and/or flash memory (e.g., NAND, NOR). The memory 508 can store an operating system, such as Darwin, RTXC, LINUX, UNIX, OS X, WINDOWS, or an embedded operating system such as VxWorks. The operating system may include instructions for handling basic system services and for performing hardware dependent tasks. In some implementations, the operating system can be a kernel (e.g., UNIX kernel).

The memory 508 may also store application programs 510-512 which act, in conjunction with the processors 504, to cause the mobile device to operate to perform certain functions, including the medical monitoring related functions described herein.

The memory 508 can also store data, including but not limited to documents, images, video files, audio files, and other data. In some implementations, the memory 508 stores address book data, which can include contact information (e.g., address, phone number, etc.) for one or more persons, organizations, services, or entities. For example, in some embodiments, the memory stores insurance policy numbers or other unique identifiers to allow a user of the mobile device 500 to quickly access insurance policy related data and information. In some embodiments, medical data collected under control of the medical monitoring application may be stored in the memory 508 (either temporarily or for longer periods).

In some embodiments, the mobile device 500 includes a positioning system. In some embodiments, the positioning system can be provided by a separate device coupled to the mobile device 500, or can be provided internal to the mobile device. In some implementations, the positioning system can employ positioning technology including a GPS, a cellular grid, URIs or any other technology for determining the geographic location of a device. In some implementations, the positioning system can employ a service provided by a third party or external positioning. In other implementations, the positioning system can be provided by an accelerometer and a compass using dead reckoning techniques. In such implementations, the user can occasionally reset the positioning system by marking the mobile device's presence at a known location (e.g., a landmark or intersection). In still other implementations, the user can enter a set of position coordinates (e.g., latitude, longitude) for the mobile device. For example, the position coordinates can be typed into the phone (e.g., using a virtual keyboard) or selected by touching a point on a map. Position coordinates can also be acquired from another device by syncing or linking with the other device. In other implementations, the positioning system can be provided by using wireless signal strength and one or more locations of known wireless signal sources to provide the current location. Wireless signal sources can include access points and/or cellular towers. Other techniques to determine a current location of the mobile device 500 can be used and other configurations of the positioning system are possible.

Figure 6:
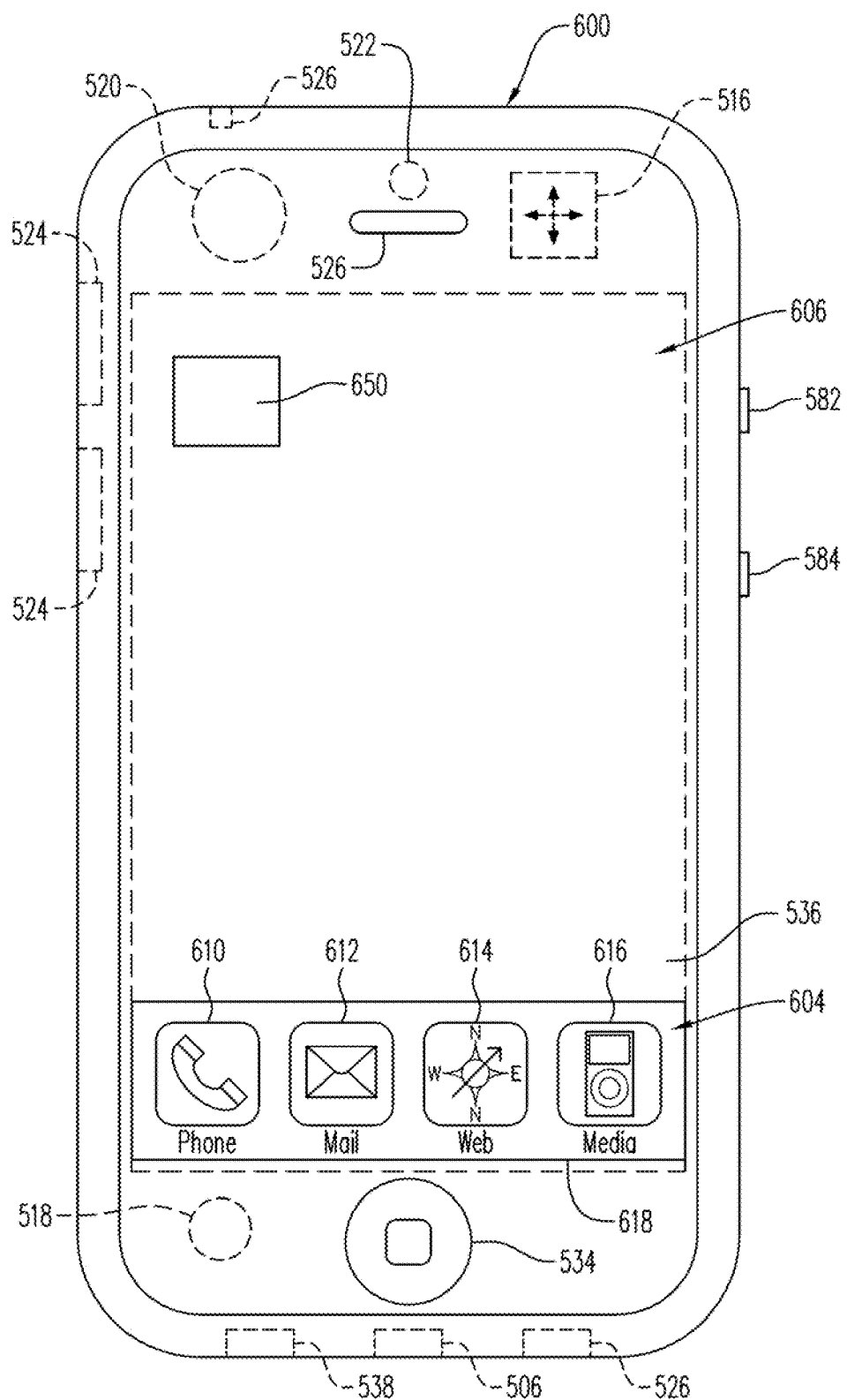
FIG. 6 is a block diagram of the mobile device of FIG. 5.

Reference is now made to FIG. 6, where a mobile device 500 is shown. As shown, the mobile device 500 can launch (and operate under the control of) one or more application programs by selecting an icon associated with an application program. As depicted, the mobile device 500 has several application programs (and corresponding icons), including an medical monitoring application (launched by selecting icon 650), a phone application (launched by selecting icon 610), an email program (launched by selecting icon 612), a Web browser application (launched by selecting icon 614), and a media player application (launched by selecting icon 604). Those skilled in the art will recognize that mobile device 500 may have a number of different icons and applications, and that applications may be launched in other manners as well (e.g., using hot keys, drop down selectors, or the like). For example, a user may have more than one medical monitoring application installed (e.g., such as one medical monitoring application configured to collect and transmit blood pressure data from a blood pressure sensor, and another medical monitoring application configured to collect and transmit blood glucose data from a blood glucose sensor, etc.). In some embodiments, a single medical monitoring application may be capable of collecting and transmitting data associated with a number of different medical sensors (e.g., a single application may be capable of controlling the collection and transmission of two or more different types of medical data). In the embodiment shown, an application, such as the medical monitoring application, is launched by the user tapping or touching an icon displayed on the touch screen 536 interface of the mobile device 500.

Once an application is launched, the user may interact with the application, and the mobile device may function pursuant to the program instructions associated with the application. In the medical monitoring applications described herein, details of some aspects of the operation of the mobile device 500 are described, however, those skilled in the art will appreciate that a number of different functions and operational features may be provided.

Figure 7A:
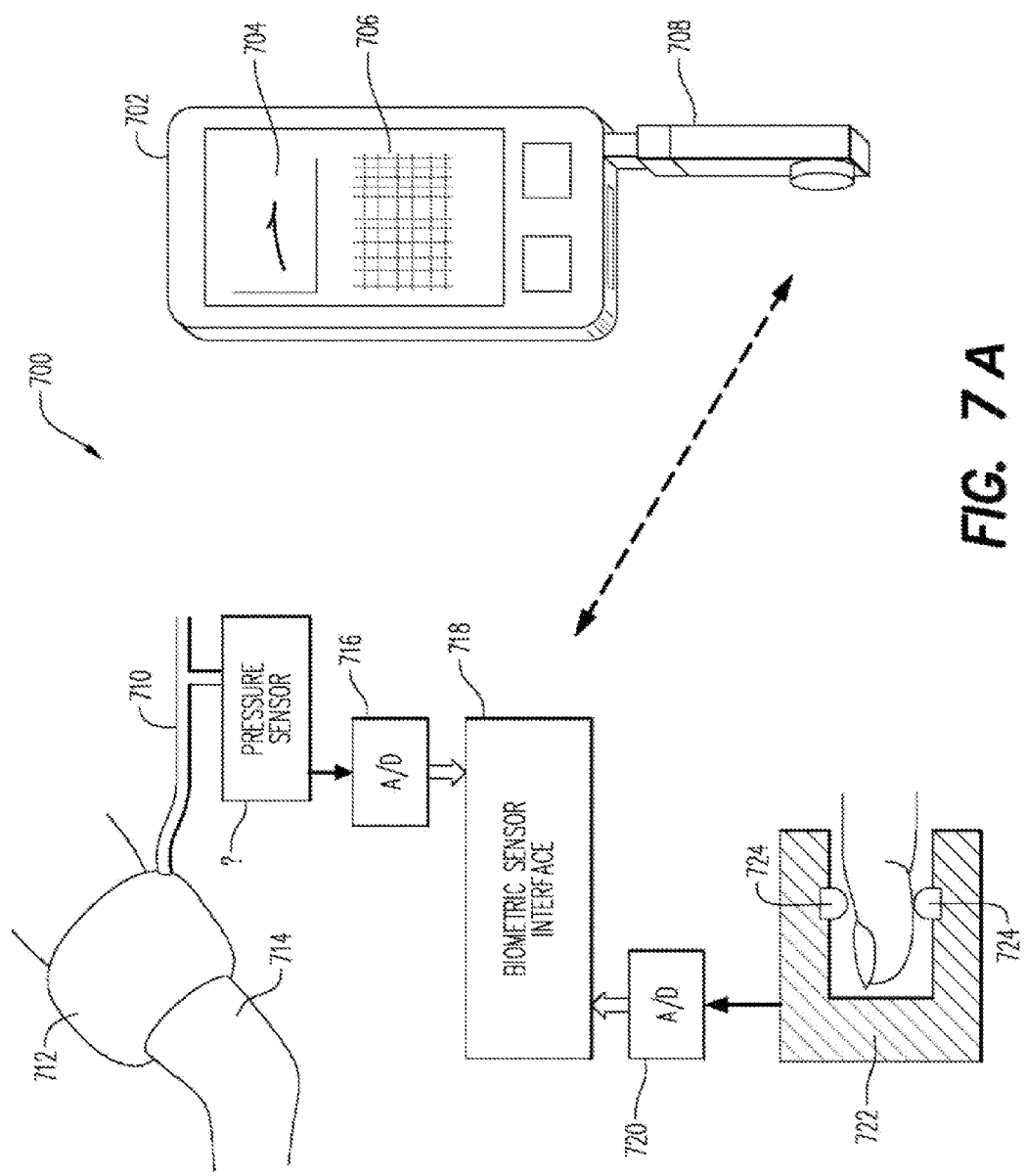
FIGS. 7A-7C are block diagrams depicting medical monitoring device and sensor configurations pursuant to some embodiments.
Figure 7B:
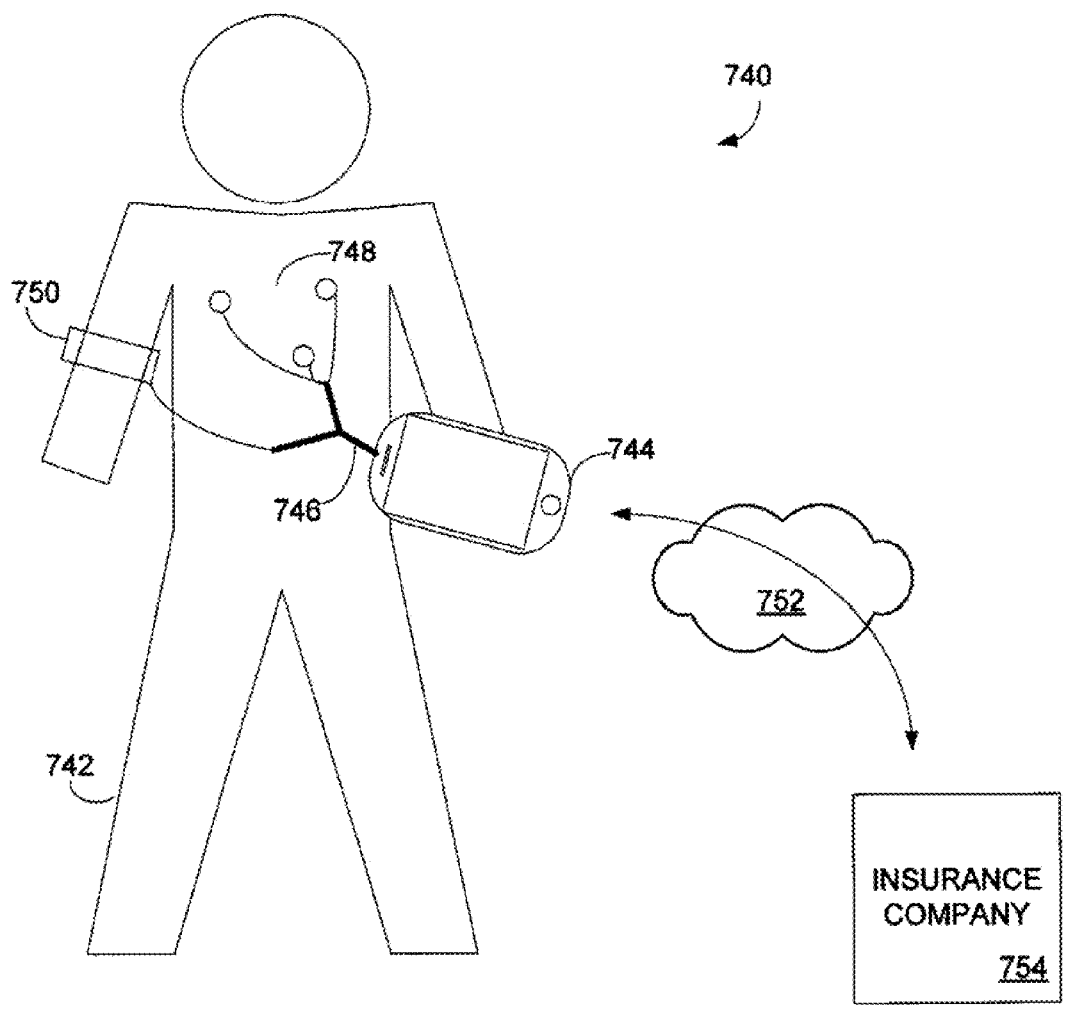

Reference is now made to FIG. 7A, which shows a block diagram 700 of a medical monitoring device and sensor pursuant to some embodiments. In the specific embodiment depicted in FIG. 7A, a mobile device 702 is in communication with a biometric sensor interface 718 for receiving blood pressure data from one of two different pressure sensors—a fingertip blood pressure sensor 722, and a cuff sensor 715. In use, only one of the two different pressure sensors 715, 722 may be used (e.g., a user may have either the fingertip sensor 722 or the blood pressure cuff sensor 712, but likely not both). Either of the sensors may be in communication with a biometric sensor interface 718 via an A/D converter 716, 720 to provide digital sensor data to the biometric sensor interface 718 for transmission to a transponder 708 attached to mobile device 702. The communication between the transponder 708 and the biometric sensor interface 718 may be any of a number of different communication techniques, including, for example a wired or a wireless interface.

The mobile device 702 has a medical monitoring application installed thereon (e.g., pursuant to the process described above in conjunction with FIG. 4), and is operable to control and receive biometric data from the biometric sensor interface 718. In some embodiments, the medical monitoring application installed on the mobile device 702 includes a user interface including a graphical overlay 704 or other depiction of data 706 received from the biometric sensor interface 718 so that a user may view and monitor the progress of data collection.

Pursuant to some embodiments, a user operating mobile device 702 may first launch the medical monitoring application and then follow a series of prompts or screen displays which instruct the user how to attach and begin the collection of data. The prompts or screen displays may instruct the user to attach the collar 712 or insert their fingertip into the sensor 722 (depending on which sensor hardware the user has installed). A configuration or initial data collection stage may be initiated once blood pressure data is detected by the mobile device 702. Once the correct data is being received, the medical monitoring application may begin the collection of data pursuant to stored rules associated with the medical monitoring application. The stored rules may vary based on the specific condition or medical issue being monitored for the specific user. For example, one user may be required to provide 30 seconds of monitoring each day, while another user may be required to provide 60 seconds of monitoring. Once the required amount of data has been collected, a user interface or series of prompts may be displayed to the user instructing the user how to disconnect or complete the medical monitoring process. The medical monitoring application may then automatically transmit the collected data, along with any user verification information, time stamps, and geographical data, to a remote insurance provider or other service provider for further analysis.

The data collected, and the rules governing the collection of that data (including the amount, frequency and number of collections), may be specified by business rules applied by business logic computer 322 of insurance company 320 (of FIG. 3). For example the rules may be rules associated with the collection of blood pressure data for the evaluation of an application for a life insurance policy, and the rules may include those identified in Table I above (e.g., where the measured blood pressure and the user's age may be used to determine whether the user qualifies for a "super preferred" risk or some other policy level). The rules may also specify that one or more feedback or informational messages be transmitted to the user after the data has been collected. For example, in a situation where the user's blood pressure has shown an improvement since a prior reading was taken, a message congratulating the user on their progress may be transmitted. As another example, in a situation where the reading shows degradation or worsening of the blood pressure numbers, a message instructing the user to review information about reducing their blood pressure (as well as links or the actual information) may be provided.

Reference is now made to FIG. 7B where a block diagram 740 depicts a user 742 operating a mobile device 744 to collect medical or health status related data for transmission to a remote insurance company 754 through a network 752. In the embodiment depicted, two different sensor devices are coupled to the mobile device 744—a set of EKG sensors 748 and a blood pressure monitor 750. The two different sensor devices 744, 750 are shown as being coupled to the mobile device 744 via a wired connection (e.g., such as a "Y" connector 746 inserted into a USB port of the mobile device 744). In the embodiment of FIG. 7B, multiple sets of medical data may be collected at the same time to collect or monitor different types of medical data such as the user's EKG and the user's blood pressure. Further, the configuration may be used to also authenticate an identity of the user (e.g., by comparing detected electrocardiogram information with a stored pattern to verify the user's identity). The identity and the medical data may be collected and transmitted to the remote insurance company 754 (or other entity) for further processing.

The data collected, and the rules governing the collection of that data (including the amount, frequency and number of collections), may be specified by business rules applied by business logic computer 322 of insurance company 320 (of FIG. 3). For example the rules may be rules associated with the collection of blood pressure data and cardiovascular data for the evaluation of an application for a life insurance policy, and the rules may include those identified in Table I above (e.g., where the measured blood pressure, the user's age, and the measured EKG data may be used to determine whether the user qualifies for a "super preferred" risk or some other policy level).

Figure 7C:
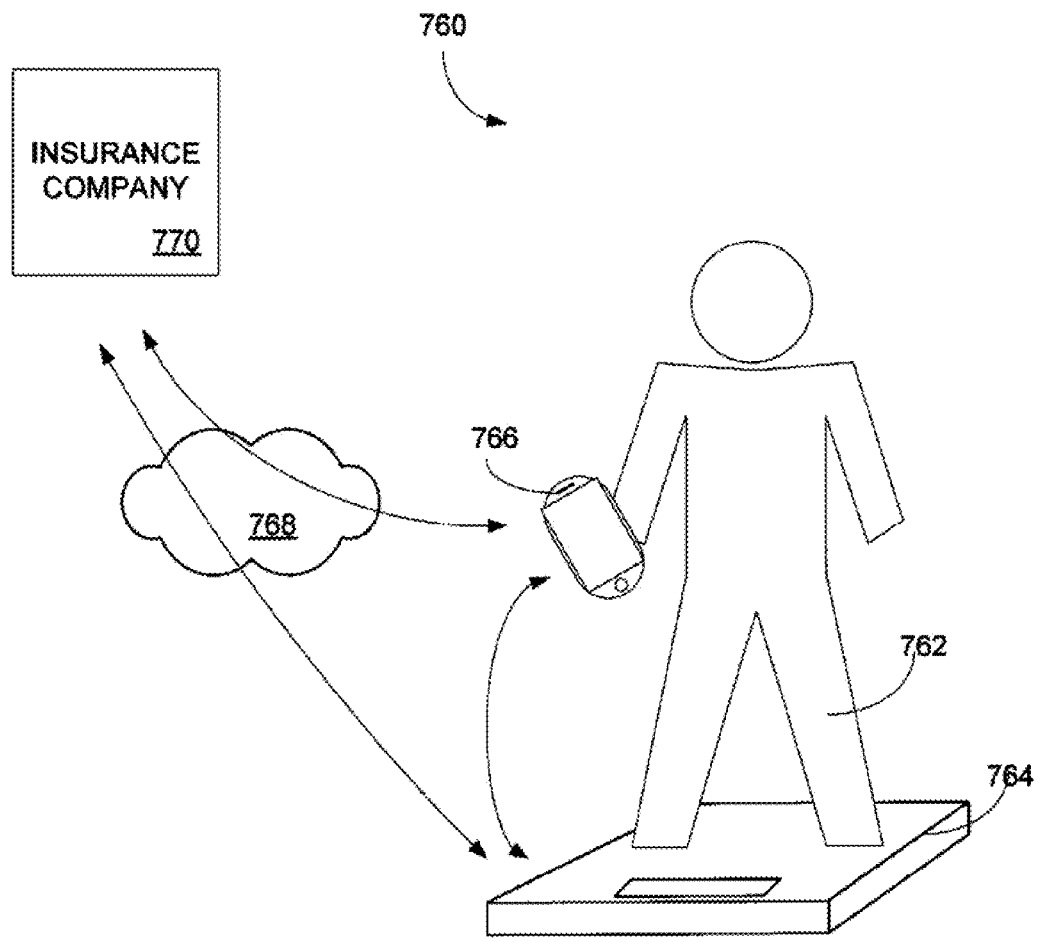

Reference is now made to FIG. 7C where a further block diagram 760 is shown in which a user 762 is operating a mobile device 766 to collect health status related data for transmission to a remote insurance company 770 via a wireless network 768. In particular, the user 762 is standing on a wireless-enabled scale 764 (such as the Withings® Internet scale available at www.withings.com) to measure the user's weight and/or body mass index ("BMI"). Both the mobile device 766 and the scale 764 are shown as being in communication with the remote insurance company 770 via a network 768. In some embodiments, the network 768 may be or include both a cellular network (over which the mobile device 766 may communicate) and a WiFi network (over which the scale 764 and/or the mobile device 766 may communicate). In some embodiments, the mobile device 766 and the scale 764 are also in communication. For example, prior to taking the weight and/or BMI measurements, the user 762 may launch a mobile application on the mobile device 766 and establish a communication session between the mobile device 766 and the scale 764. The communication session may include an authentication sequence whereby the user 762 authenticates his identity prior to standing on the scale 764. The weight and/or BMI data collected by the scale 764 may then be communicated to the mobile device 766 for transmission to the insurance company 770 or may be communicated directly to the insurance company 770 for processing.

The data collected, and the rules governing the collection of that data (including the amount, frequency and number of collections), may be specified by business rules applied by business logic computer 322 of insurance company 320 (of FIG. 3). For example the rules may be rules associated with the collection of weight and BMI related data for the evaluation of an application for a life insurance policy, and the rules may include those identified in Table I above (e.g., where the measured weight and BMI data may be used to determine whether the user qualifies for a "super preferred" risk or some other policy level). The rules may also specify that one or more feedback or informational messages be transmitted to the user after the data has been collected. For example, a user who has lost weight since a prior reading may be presented with a congratulations message (or an incentive or reward). A user who is having trouble losing weight or who has gained weight may be given feedback and information on how to improve their weight loss progress.

Those skilled in the art will appreciate that a variety of other sensors, measurement devices, and communication paths may be used to collect medical and health status related data from users who are interacting with insurance companies, thereby allowing insurers to more accurately assess risk and administer and management insurance policies.

Those skilled in the art will appreciate that a wide variety of other types of medical data may be collected and transmitted for analysis pursuant to the present invention. By collecting such information under control of a medical monitoring application provided by an insurer or other entity, the appropriate amount and type of medical data needed to make insurance underwriting, pricing and other decisions may be consistently and accurately made by an insurer. Further, because embodiments control the collection and transmission of such data, remote users may be entrusted with the collection of data in the convenience of their own homes or places of work without the need to visit medical testing companies or their doctor.

The data collected using such techniques may be used by insurance providers and other entities to make insurance related decisions where legally allowed. For example, referring now to FIG. 8, a flow chart is depicted providing a number of exemplary steps in a method 800 for evaluating data received from a mobile device operating one or more medical monitoring applications as described above. For example, in embodiments where a mobile device is configured to collect medical or health status-related data associated with a user, the data may be collected, transmitted and used to evaluate insurance premiums and policy adjustments using the method of FIG. 8.

Figure 8:
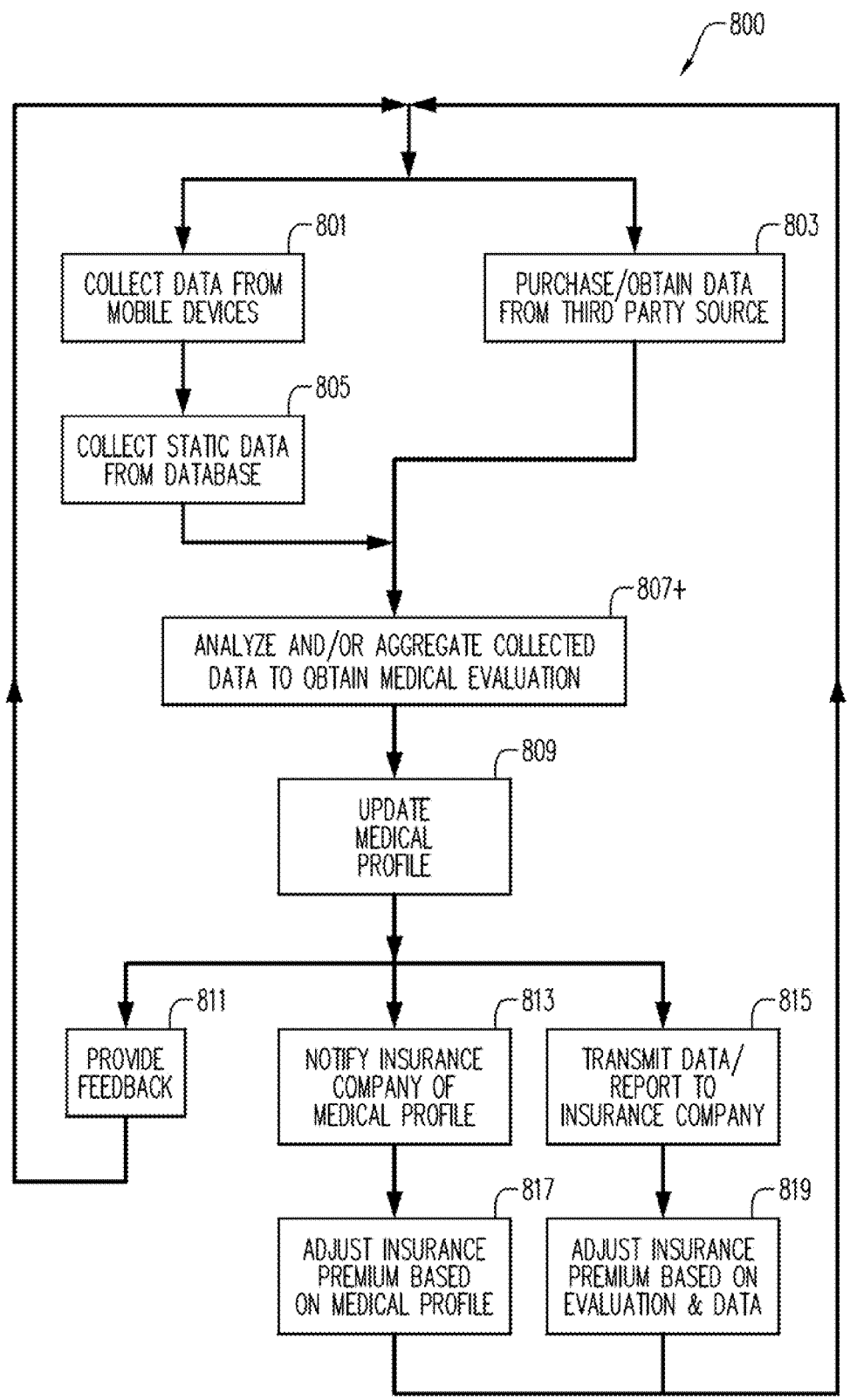
FIG. 8 is a flow diagram depicting a process for evaluating mobile device data pursuant to some embodiments.

The method of FIG. 8 begins at 801 by collecting data from mobile devices associated with an insured customer (or, in some embodiments, associated with a prospective insured customer). The data may include medical or health status-related data collected under control of a medical monitoring application in conjunction with one or more sensors. The data may be transmitted to an insurance system for processing via wireless or cellular communication protocols. In some embodiments, the data may be transmitted automatically under control of a mobile application installed or operated on a mobile device associated with the customer.

In addition to mobile device data, static data may be collected at 805. Static data may include personal information associated with a customer, such as their medical history, level of physical fitness, etc. In addition to or instead of collecting data from mobile devices and local static data servers, data may also be purchased or obtained from a third party at 803. The purchased data may be used to supplement the mobile device data or may be used to validate or debug the system.

The data is analyzed, processed, and aggregated at 807. The aggregated data may be generated into reports, which can then be provided to interested parties (at 811 below). Data processing may include applying algorithms to the collected data, which may be in its raw form, to obtain values of interest. For example, raw sensor data may be noise filtered or otherwise analyzed to determine patterns or trends. In response to an insured customer providing the medical data, the insurance company can favorably alter the terms of the insurance policy, such as decreasing the premium or deductible.

At 813, the insured customer provides the medical monitoring data to the insurance company. In some embodiments, simply based on the customer's willingness to provide the data, and without receiving the actual data, the insurance company may grant discounts to the insured at 817 (e.g., such willingness to provide the data may indicate a person's desire to improve or maintain their health status and may entitle them to a discount). In deciding to alter the terms of the insurance policy, the insurance company, or a third party evaluator, may compare the mobile device data, as determined from the mobile device, of the insured to a comparative baseline. The process of FIG. 8 may be repeated on a regular basis, and a similar process may be applied for a plurality of insured customers. In some embodiments, the process may be used to price and issue policies for new customers as well.

Figure 9:
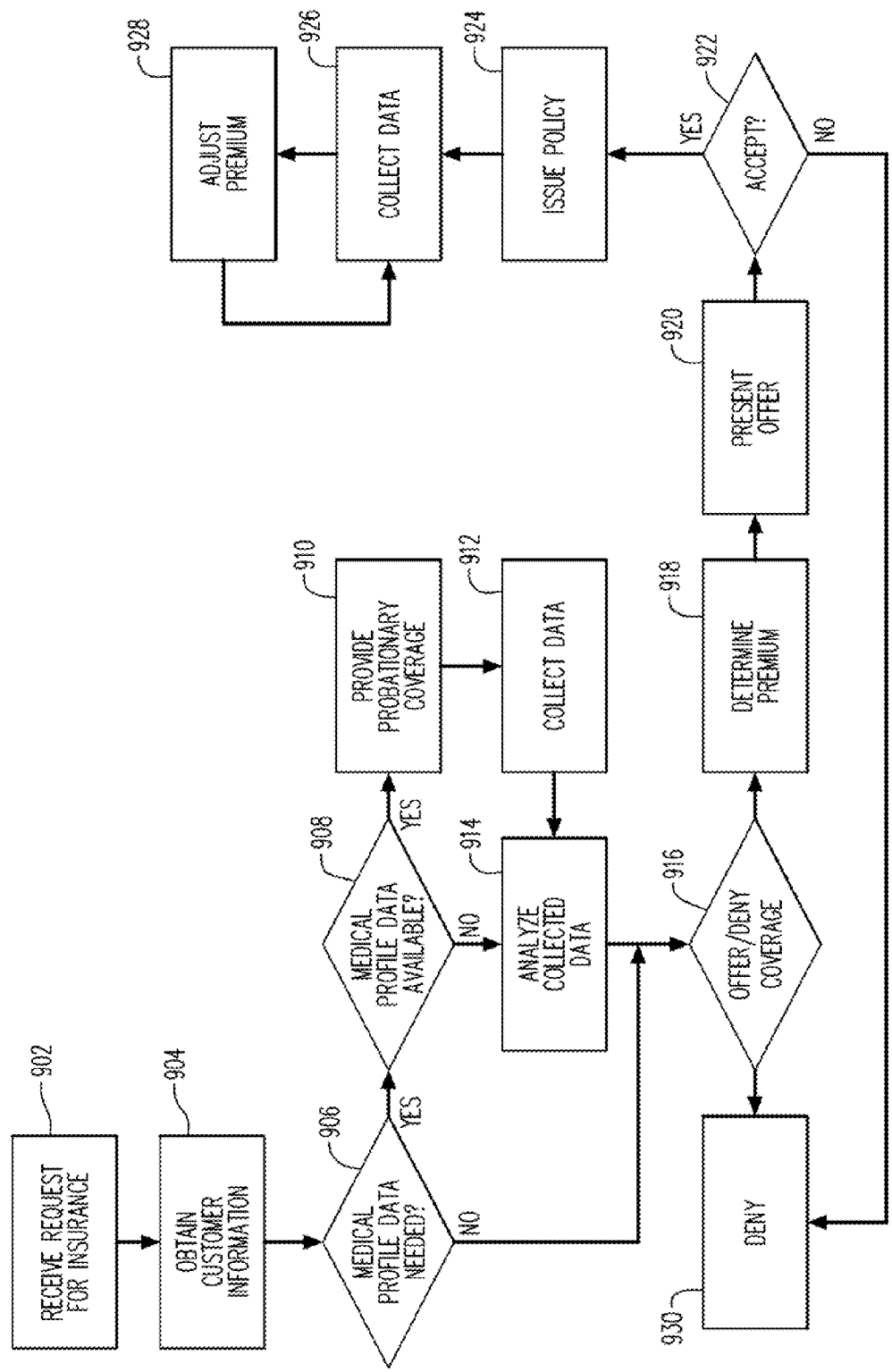
FIG. 9 is a flow diagram of a process carried out by the system of FIG. 1 for processing requests for insurance.

Reference is now made to FIG. 9 which is a high level flow chart of a method carried out by the system of FIG. 3 in processing requests for insurance. The method begins at 902 with the receipt of a request to insure an individual. As described above, the request may be received by an insurance company 920 from a mobile device (such as the mobile device 500 described in conjunction with FIGS. 5 and 6) or an agent/employee terminal. The system then requests and obtains information about the customer and the customer's medical status or health 904. The information is obtained in part through requests posed to the customer or insurance agent or employee assisting the customer. Additional information is obtained through third party data vendors 307 and/or from the insurance company's central database 304. Pursuant to some embodiments, many of the questions posed to the customer are presented to the consumer by an application on the mobile device which is provided by the insurance company.

In some situations, a prospective insured customer may be required to agree to provide medical monitoring data associated with the customer's health status or health patterns in order to qualify for a policy (or to qualify for good health discounts, etc). Insurance products that incorporate the use of collected medical monitoring data in pricing and underwriting enable insurance companies to insure customers that might otherwise be outside of their appetite. That is, the risks presented by insuring a particular customer or medical condition may be too large for an insurance company to accept unless it is actively able to monitor the current status of the health of the customer. Thus, in one embodiment, after obtaining basic information about the customer at 904, the system 320 determines whether medical monitoring data is needed for making a final insurability decision at 906. The system may determine that medical monitoring data is unnecessary, for example, if the insurer determines that no amount of health or medical data will bring the requested policy within the appetite of the insurance company, resulting in the request for coverage being denied at 916.

Insurance products using collected medical or health status-related data for adjusting premiums may also be used to reward customers that maintain or improve their medical conditions. Thus, in some circumstances, collection of medical data is not necessary, but instead is merely an option provided to customers that may lead to lower premiums. In such situations, the decision at 906 may be skipped, and the method proceeds directly from the receipt of basic customer information (at 904) to determining whether medical monitoring data is available (at 908).

If at determination at 908 indicates that existing medical condition data is not available the insurance company, in one embodiment, may offer the customer insurance during a probationary period (at 910) during which the insurance company can obtain baseline driving medical condition data (at 912) on which it can base its underwriting and pricing decision. Depending on the health profile or characteristics of the consumer and/or the data collected during the probationary period, the probationary period may vary in length, for example, from about one to about three months. For example, if the medical data collected in a first month exhibits a great deal of variability, the period may be extended. The medical data can include a number of parameters depending on the type of health condition(s) the customer exhibits. For example, for serious conditions presenting a high degree of risk, the monitored health conditions can include the collection of data from a variety of different sensors (e.g., such as, for a diabetic, blood pressure data collected using a blood pressure sensor, and blood glucose data collected using a blood glucose monitor). The type of conditions monitored may also dictate the frequency and timing of collection of the data. Pursuant to some embodiments, each condition, and the collection of data for the condition, may be defined using one or more rules embodied in the medical monitoring application provided to the customer.

The premium offered by the insurance company during the probationary period is likely higher than the premium that would be paid during a non-probationary coverage period, unless the data collected during the probationary period suggests the risks of issuing a non-provisional policy are substantially higher than expected based on the information collected prior to the probationary policy. Pursuant to some embodiments, the use of such a probationary period may be used in conjunction with an "issue first" type of policy in which a customer is provisionally issued a policy based on data collected from the customer at 904 (e.g., such as a medical survey or history).

The insurance company 320 then analyzes the medical monitoring data made available at 908 or collected at 912 (at 914). The exact analysis process, as described further below, is determined dynamically based on the nature of the data collected, information about the customer, and/or information about the condition being monitored. For example, the analysis may take into account different monitored parameters or take into account the same parameters to different extents. Preferably, the analysis is carried out using one or more predictive models, such as statistical models, neural networks, expert systems, or other forms of artificial intelligence.

Based on the analysis carried out at 914, the insurance company 320 decides whether to offer insurance to the customer under the terms requested by the customer (at 916), and if so, calculates a premium for such a policy (at 918). The premium may be calculated holistically for an entire policy, or separately for each coverage requested in the policy. In one embodiment, the analysis of collected data at 914, the decision to offer or deny insurance at 916, and the determination of a premium at 918 constitute a single process carried out by the computing systems of the insurance company 320. In alternative implementations, the underwriting decision and the pricing calculation are carried out separately in series.

After determining a premium for the policy at 918, the system forwards an offer for insurance to the mobile device 330 or employee/agent terminal 305 (at 920). If the customer rejects the offer (at 922), for example, due to the premium being higher than desired, or if the insurance company 320 declines to offer insurance (at 916), the process ends. If the offer is accepted (at 922), the insurance company issues an insurance policy covering the customer (at 924). After the policy is issued, the insurance company 320, either directly or through a monitoring service, may continue to monitor the output of the medical monitoring application and the sensors associated with the mobile device 330. Based on the results of the monitoring, the insurance company 320 occasionally or periodically may adjust the premium charged to the customer. The premium change, if any, preferably uses the same artificial intelligence used to set the initial premium. The premium change may affect the premium charged in future periods, in prior periods, e.g., through issuance of a refund or surcharge, or in a current period, depending on the specific implementation of the method. Alternatively, the premium change may only affect the premium charged for a renewal policy after the expiration of the current policy term. In some embodiments, some of the data collected may be collected at a third party location such as a "minute clinic" or other outpatient testing location. In some embodiments, the results of the third party data collection may be entered into the mobile device 330 for transmission to the insurance company 320. As a specific example, in situations where a blood test or other laboratory testing is required, a customer may take the mobile device 330 (with the medical monitoring application installed) to a certified laboratory or minute clinic, and present the testing instructions to the laboratory or clinic using the mobile device 330. The clinic, upon completion of the specified testing, may then enter the test results into the mobile device 330 to fulfill the testing requirement.

Thus, embodiments of the present invention may improve the information available to insurers to allow them to better price, underwrite and administer insurance policies that are based on or related to a customer's health status. Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

What is claimed is:

1. An insurance system, comprising:
    a data storage device for storing, updating and providing access to data defining a plurality of medical monitoring rules;
    a computer processor for executing program instructions and for retrieving said medical monitoring rule data from the data storage device;
    a memory, coupled to the computer processor, for storing program instructions for execution by the computer processor to
        process an insurance request message, said insurance request message including data identifying an insurance request from a user associated with a mobile device;
        determine that said insurance request is associated with at least one medical monitoring rule;
        generate an insurance monitoring request for transmission to said user associated with said mobile device, said insurance monitoring request including data identifying a medical monitoring application to be installed on said mobile device and operated to collect medical data from said user associated with said mobile device said insurance monitoring request and said medical monitoring application selected based on said at least one medical monitoring rule;
        receiving information associated with said medical data collected from said mobile device operating said medical monitoring application; and
        generating a response to said insurance request message based at least in part on said medical data.

2. The insurance system of claim 1, further comprising:
    an insurance determination module, coupled to a computer processor, and storing program instructions for execution by the computer processor to adjust a premium associated with an insurance policy based at least in part on said medical data.

3. The insurance system of claim 1, further storing program instructions for execution by the computer processor to:
    apply said at least one medical monitoring rule to said medical data collected from said mobile device to determine a premium level for said user.

4. The insurance system of claim 1, further storing program instructions for execution by the computer processor to:

provide, to said medical monitoring application of said mobile device associated with said user, instructions to collect further medical data associated with said at least one medical monitoring rule; and
receive further information associated with said further medical data collected from said mobile device operating said medical monitoring application.

5. The insurance system of claim 1, further storing program instructions for execution by the computer processor to:
    generate information for transmission to said medical monitoring application of said mobile device associated with said user, said information for presentation to a user of said mobile device, and said information associated with said medical data received from said mobile device.

6. The insurance system of claim 1, wherein said medical monitoring rule is associated with at least two types of insurance coverages, at least one of which is a life insurance coverage.

7. A method for operating a mobile device, comprising:
    installing a medical monitoring application associated with a user of said mobile device, said medical monitoring application including configuration data associated with at least a first medical monitoring rule, said medical monitoring application and said configuration data generated by an insurance company in response to an insurance request by said user;
    displaying, under control of said medical monitoring application, a series of instructions to cause said mobile device to be configured to communicate with at least a first biometric sensor;
    collecting, based on said at least first medical monitoring rule, a set of biometric data from said at least first biometric sensor; and
    transmitting said set of biometric data from said mobile device to a remote processing system.

8. The method of claim 7, wherein said at least first medical monitoring rule specifies at least one of a frequency and a schedule of said collecting a set of biometric data.

9. The method of claim 7, wherein said medical monitoring application further includes at least a first verification rule.

10. The method of claim 9, the method further comprising:
    collecting, based on said at least one verification rule, verification data to verify an identity of said user prior to said collecting said set of biometric data.

11. The method of claim 10, further comprising:
    transmitting said verification data with said set of biometric data to said remote processing system.

12. The method of claim 10, wherein said verification data is based at least in part on biometric data associated with said user.

13. The method of claim 7, wherein said medical monitoring application further includes configuration data associated with a second medical monitoring rule, the method further comprising:
    displaying, under control of said medical monitoring application, a series of instructions to cause said mobile device to be configured to communicate with a second biometric sensor;
    collecting, based on said at least second medical monitoring rule, a second set of biometric data from said second biometric sensor; and
    transmitting said set of biometric data and said second set of biometric data to said remote processing system.

14. The method of claim 7, wherein said first biometric sensor is configured to communicate with said mobile device using at least one of a wireless or a wired interface.

15. A computer-implemented insurance processing method, comprising:
- receiving, by a computer system, an insurance request from a user, said insurance request including data identifying a medical condition of said user;
- determining that medical data associated with said user and said medical condition is required to process said insurance request;
- identifying, based on said medical condition, at least a first medical monitoring rule;
- providing, to a mobile device associated with said user, a medical monitoring application including configuration data associated with said at least first medical monitoring rule for operation on said mobile device associated with said user;
- receiving, from said mobile device, biometric data associated with said first medical monitoring rule; and
- processing, by a computer system, said insurance request based on said data identifying a medical condition, said first medical monitoring rule, and said biometric data.

16. The computer-implemented insurance processing method of claim 15, wherein said insurance request is a request for a new insurance policy.

17. The computer-implemented insurance processing method of claim 15, wherein said insurance request is a request for a renewal of an existing insurance policy.

18. The computer-implemented insurance processing method of claim 15, wherein said configuration data associated with said at least first medical monitoring rule defines a frequency and schedule associated with the collection of said biometric data.

19. The computer-implemented insurance processing method of claim 15, further comprising generating at least a first user verification rule, wherein said medical monitoring application further includes configuration data for applying said at least first user verification rule.

20. The computer-implemented insurance processing method of claim 19, wherein said receiving said biometric data further comprises receiving verification data based on said at least first user verification rule, the method further comprising:
- verifying an identity of said user based on said verification data.

21. A portable wireless communication device, comprising:
- a touch-sensitive display screen;
- a communication port;
- a processor;
- a memory;
- and a program, wherein the program is stored in the memory and configured to be executed by the processor, the program including:
  - instructions for presentation to a user of said device, said instructions defining a sequence of steps to configure a sensor for use with said device, the instructions established based on configuration data defined by at least a first medical monitoring rule identified in response to an insurance request by said user;
  - instructions for collecting data from said sensor, said instructions including information specifying a schedule for said collecting and information specifying a user authentication process, the schedule for said collecting based on configuration data defined by said at least first medical monitoring rule; and
  - instructions for transmitting said collected data and said results of said user authentication process to a remote insurance processing system using said communication port.

22. The device of claim 21, further comprising:
instructions for receiving a response message from said remote insurance processing system using said communications port, said response message including instructions for collecting further data from said sensor.

23. A computer-implemented insurance processing method, comprising:
- receiving, at an insurance computer system, an insurance request associated with a policy covering a plurality of individuals, said insurance request including data identifying said plurality of individuals and an associated medical condition of said individuals;
- determining that medical data associated with said plurality of individuals and said associated medical condition is required to process said insurance request;
- identifying, based on said medical condition, at least a first medical monitoring rule;
- providing, to a plurality of mobile devices associated with said plurality of individuals, a medical monitoring application including configuration data associated with said at least first medical monitoring rule for operation on said plurality of mobile devices associated with said plurality of individuals;
- receiving, from each of said plurality of mobile devices, biometric data associated with said first medical monitoring rule collected from each of said plurality of individuals; and
- processing said insurance request based on said data identifying a medical condition, said first medical monitoring rule, and said biometric data.

24. The computer-implemented insurance processing method of claim 23, wherein said insurance request is a request for a new insurance policy.

25. The computer-implemented insurance processing method of claim 23, wherein said insurance request is a request for a renewal of an existing insurance policy.

26. The computer-implemented insurance processing method of claim 23, wherein said configuration data associated with said at least first medical monitoring rule defines a frequency and schedule associated with the collection of said biometric data.

27. The computer-implemented insurance processing method of claim 23, wherein said policy is at least one of a group benefits policy, a workers compensation policy and a commercial insurance policy.

* * * * *